United States Patent [19]
Skubitz et al.

[11] Patent Number: 6,013,628
[45] Date of Patent: Jan. 11, 2000

[54] METHOD FOR TREATING CONDITIONS OF THE EYE USING POLYPEPTIDES

[75] Inventors: Amy P. N. Skubitz; Leo T. Furcht, both of Minneapolis, Minn.; Mark Balles, Indianapolis, Ind.; Dale S. Gregerson, Minneapolis, Minn.; Anita Agarwal, Gainesville, Fla.; Martha M. Wright, St. Paul; Shobana Murali, Roseville, both of Minn.

[73] Assignee: Regents of the University of Minnesota, Minneapolis, Minn.

[21] Appl. No.: 08/394,748

[22] Filed: Feb. 27, 1995

Related U.S. Application Data

[63] Continuation-in-part of application No. 08/203,458, Feb. 28, 1994, abandoned.

[51] Int. Cl.$^7$ .......................... A61K 38/00; A61K 38/02; C07K 5/00; C07K 7/00
[52] U.S. Cl. ............................... 514/12; 514/13; 514/14; 514/15
[58] Field of Search .................. 514/12, 13, 14, 514/15

[56] References Cited

U.S. PATENT DOCUMENTS

| | | |
|---|---|---|
| 4,839,464 | 6/1989 | McCarthy et al. . |
| 4,876,332 | 10/1989 | Tsilibury et al. . |
| 5,019,646 | 5/1991 | Furcht et al. . |
| 5,081,031 | 1/1992 | Tsilibary et al. . |
| 5,082,926 | 1/1992 | Chelberg et al. . |
| 5,266,328 | 11/1993 | Skubitz et al. . |

FOREIGN PATENT DOCUMENTS

91/09113  6/1991  WIPO .............................. C12N 5/00

OTHER PUBLICATIONS

Avery et al., *Arch. Opthalmol.*, vol. 104 pp. 1220–1222, 1986.
Alvira et al., *Invest. Ophthalmol. Vis. Sci.*, 27 (supp.), p. 305 (1986).
Avery et al., *Arch Ophthalmol.*, 104, pp. 1220–1222 (1986).
Bergstrom, et al., "The Effects of Subconjunctival Mitomycin–C on Glaucoma Filtration Surgery in Rabbits", *Laboratory Sciences*, 109, pp. 1725–1730, (1991).
Blumenkranz et al., In *Retina*, vol. 3, pp. 401–411, Bert M. Glaser, M.D., Ed., (1989).
Blumenkranz et al., In *Retina*, vol. 12(3S), pp. S71–74 (1992).
Chandler et al., *Graefe's Arch. Clin. Exp. Ophthalmol.*, 224, pp. 86–91 (1986).
Chelbert et al., *J. Cell Biol.*, 111, pp. 261–270 (1990).
Campochiaro et al., *Invest. Ophthalmol. Vis. Sci.*, 27, pp. 1615–1621 (1986).
Doyle, et al., "Intraoperative 5–Fluorouracil for Filtration Surgery in the Rabbit", *Invest. Ophthalmol. Vis. Sci.*, 34, pp. 3313–3319, (1993).
Fawcett, *A Textbook of Histology*, 12th ed., pp. 872–918 (1994).

Foidart et al., *Lab Invest.*, 42, 336–342 (1980).
Glaser, In *Retina*, vol. 3, pp. 385–400, Bert M. Glaser, M.D., Ed. (1989).
Gordon et al., *Cell Tissue Res.*, 244, 583–589 (1986).
Halfter et al., *Cell Tissue Res.*, 249, pp. 487–496 (1987).
Haugen et al., *J. Cell Biol.*, 111, pp. 2733–2745 (1990).
Hewick et al., *J. Biol. Chem.*, 256, pp. 7990–7997 (1981).
Hida et al., *Graefe's Arch. Clin. Exp. Ophthalmol.*, 225, pp. 303–307 (1987).
Iida et al., *J. Cell Biol.*, 118, pp. 431–444 (1992).
Johnson et al., *Invest. Ophthalmol. Vis. Sci.*, 27 (supp.), p. 186 (1986).
Kay et al., "Delivery of Antifibroblast Agents as Adjuncts to Filtration Surgery—Part II: Delivery of 5–Fluorouracil and Bleomycin in a Collagen Implant: Pilot Study in the Rabbit", *Ophthalmic Surgery*, 16, pp. 796–801, (1985).
Kitazawa et al., "Trabeculectomy With Mitomycin", *Arch. Ophthalmol*, 109, pp. 1693–1698, (1991).
Koliakos et al., *J. Biol. Chem.*, 264, pp. 2313–2323 (1989).
Kornblihtt, et al., "Primary structure of human fibronectin: differential splicing may generate at least 10 polypeptides from a single gene", *The EMBO Journal*, 4, pp. 1755–1759, (1985).
Kumar, et al., "In Situ–Forming Gels for Ophthalmic Drug Delivery", *Journal of Ocular Pharmacology*, 10, pp. 47–56, (1994).
Lee, et al., "The Effect of 5–Fluorouracil and Cytarabine on Human Fibroblasts From Tenon's Capsule", *Invest. Ophthalmol. Vis. Sci.*, 31, pp. 1848–1855, (1990).
Martin et al., *Ann. Rev. Cell Biol.*, 3, pp. 57–85 (1987).
McCarthy et al., *J. Cell Biol.*, 97, pp. 772–777 (1983).
McCarthy et al., *Biochemistry*, 27, pp. 1380–1388 (1988).
McCarthy et al., *J. Cell Biol.*, 110, pp. 777–787 (1990).
McLoon et al., *J. Neurosci.*, 8(6), pp. 1981–1990 (1988).
Mooradian et al., *Invest. Ophthalmol. Vis. Sci.*, 33, pp. 3034–3040 (1992).
Mooradian et al., *Invest. Ophthalmol. Vis. Sci.*, 34, pp. 153–164 (1993).

(List continued on next page.)

*Primary Examiner*—Avis M. Davenport
*Attorney, Agent, or Firm*—Merchant,Gould, Smith Edell, Welter & Schmidt

[57] ABSTRACT

A method is provided for treating diseases and conditions of the eye which include scarring and proliferation of fibroblasts. The invention includes a method for treating proliferative vitreoretinopathy. The invention also includes a method for treating glaucoma. One embodiment of the method includes administering to the eye an amount effective for treating such a condition of a polypeptide. The polypeptide includes a sequence of at least about 5 amino acids corresponding substantially to an amino acid sequence from within the 33 kD fragment of the A chain of fibronectin, within the G domain of the A chain of laminin, or within the NC1 domain of the α2 chain of type IV collagen. Another embodiment of the method, which includes administering to the eye an amount of conjugate including the polypeptide and a carrier molecule conjugate, is also disclosed.

26 Claims, 26 Drawing Sheets

OTHER PUBLICATIONS

Palm et al., *J. Cell Biol.,* 96, pp. 1218–1226 (1983).
Philip et al., *Invest. Ophthalmol. Vis. Sci.,* 28, pp. 1275–1280 (1987).
Sasaki et al., *J. Biol. Chem.,* 263, pp. 16536–16544 (1988).
Skubitz et al., *J. Cell Biol.,* 115, pp. 1137–1148 (1991).
Skuta, et al., "Intraoperative Mitomycin versus Postoperative 5–Fluorouracil in High–risk Glaucoma Filtering Surgery", *Ophthalmology,* 99, pp. 438–444, (1992).
Stern et al., In *Retina,* vol. 3, pp. 413–418, Bert M. Glaser, M.D., Ed. (1989).
Thresher et al., *Graefe's Arch. Clin. Exp. Ophthalmol.,* 221, pp. 192–198 (1984).
Timple et al., *Eur. J. Biochem.,* 120, pp. 203–211 (1981).
Tsilibary et al., *J. Cell Biol.,* 111, pp. 1583–1591 (1990).
Van Bockxmeer et al., *J. Tissue Culture Meth.,* 7, pp. 163–167 (1982).
Van Bockxmeer et al., In *Retina,* vol. 5(1), pp. 47–60 (1985).
Verdoorn et al., *Arch Ophthalmol.,* 104, pp. 1216–1219 (1986).
Wilke et al., *J. Invest. Dermatol.,* 95, pp. 264–270 (1990).
Wilke et al., *J. Invest. Dermatol.,* 97, pp. 141–146 (1991).
Yamada, *Cell Biology of Extracellular Matrix,* 2nd ed., pp. 111–146 (1991).

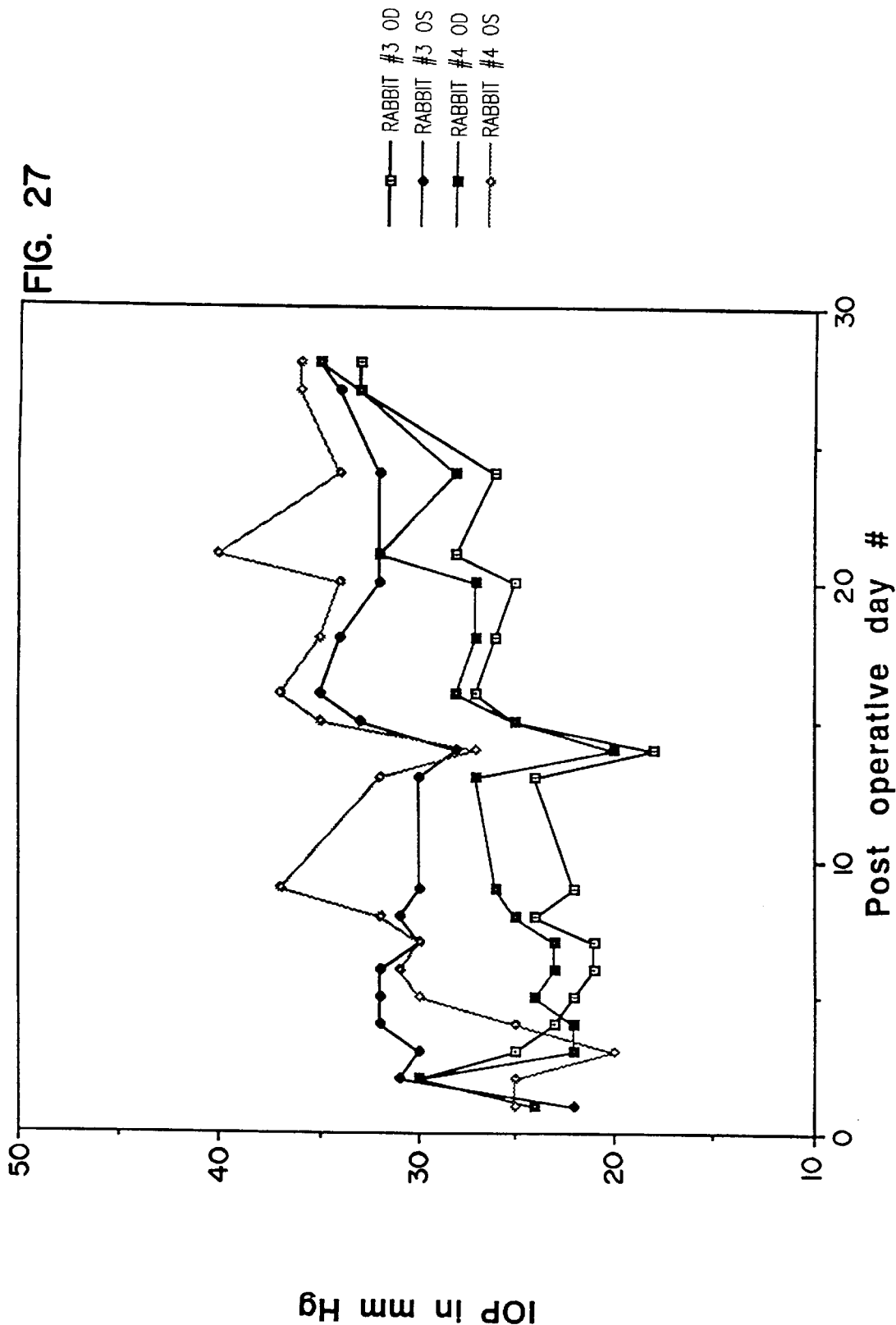

METHOD FOR TREATING CONDITIONS OF THE EYE USING POLYPEPTIDES

CROSS REFERENCE TO RELATED APPLICATION

This application is a Continuation-in-Part of application Ser. No. 08/203,458, filed Feb. 28, 1994, now abandoned.

GOVERNMENT SUPPORT

The present invention was made with the support of Grant Nos. EY-09065 and EY-09207 from the National Institutes of Health—National Eye Institute. The government has certain rights in the invention.

BACKGROUND OF THE INVENTION

Several conditions of the eye result in migration and proliferation of fibroblasts. Such conditions include injury to the tissue of the eye, retinal detachment, filtration surgery to treat glaucoma, other eye surgeries, and other insults to the tissue of the eye. These conditions are susceptible to treatment or mitigation by agents that inhibit scarring and fibroblast migration and proliferation. Migration and proliferation of fibroblasts resulting from two of these conditions, retinal detachment and filtration surgery to treat glaucoma, is well characterized. In vitro and in vivo model systems have been developed for proliferative vitreoretinopathy that can result from retinal detachment. Scarring and bleb formation that can result from filtration surgery to treat glaucoma has also been studied using in vitro and animal models. Results of tests of therapeutic agents in these in vitro and in vivo models correlate with clinical results in humans. Given the wide involvement of scarring and fibroblast proliferation in degradation of vision, there exists a need for agents that ameliorate this degradation by mechanisms which include the inhibition of scarring and fibroblast proliferation.

Proliferative Vitreoretinopathy

Severe proliferative vitreoretinopathy (PVR) occurs in approximately 10% of patients who develop retinal detachment, and is the major cause of unsuccessful retinal reattachment surgery, leading to persistent retinal detachment and permanent loss of vision. Clinically, patients with early stages of proliferative vitreoretinopathy show increased haze and turbidity in the vitreous gel, indicating the presence of proliferating fibroblasts, retinal pigmented epithelial cells (RPE), and glial cells. This early stage of proliferative vitreoretinopathy is classified as Grade A. As these cells attach to the extracellular matrix (ECM) proteins on the retinal surface, the edge of the retinal tear becomes rolled as the cells begin to contract (Grade B). Later, as epiretinal membrane contraction progresses, fixed retinal folds develop (Grade C; folds in one quadrant=C1; folds in two quadrants=C2; folds in three quadrants=C3). These are typically most prominent in the inferior equatorial region due to gravity causing proliferating cells to settle and attach to the retinal ECM proteins in these locations.

As the clinical disease progresses, it is typically associated with total retinal detachment and fixed retinal folds due to the contraction of epiretinal membranes in all four quadrants (Grade D). This may be accompanied by antero-posterior foreshortening of the retina, caused by adhesion, proliferation and contraction of epiretinal membranes over the anterior retina and ciliary body, dragging the peripheral retina over the pars plana, ciliary body, and even onto the posterior surface of the lens.

If the disease process continues, the geometry of the retinal detachment progresses from an open to a closed "funnel" configuration; basically a scarred stalk of retina extending from the optic nerve anteriorly through the middle of the vitreous cavity to its anterior attachment behind the lens (see FIGS. 1 and 2). Untreated, retinal detachment results in permanent blindness. Even with the best of treatment, the visual prognosis is markedly diminished once significant proliferative vitreoretinopathy (grade C2 or greater) develops.

Conventional scleral buckling surgery can be used to repair most rhegmatogenous retinal detachments which are not associated with or have only minimal proliferative vitreoretinopathy. Retinal detachment associated with significant proliferative vitreoretinopathy (Grade C2 or greater) has a poor surgical outcome with conventional surgical techniques alone. Over the past fifteen years, techniques have been developed which allow some of these previously inoperable eyes to be salvaged. The current treatment for proliferative vitreoretinopathy includes conventional surgical techniques to support the peripheral retina and anterior vitreous base, followed by microsurgical removal of the vitreous gel and epiretinal membranes. The removal of these fine membranes from the surface of the retina is accomplished manually with 20 gauge (0.9 mm diameter) picks, forceps, scissors, and automated suction cutting instruments.

Despite many recent technological advances, such as improvement of microsurgical instrumentation, endolaser intraoperative retinal photocoagulation, and long acting intraocular tamponade agents, successful surgical retinal reattachment is currently achieved in severe proliferative vitreoretinopathy (Grade C3 or greater) in only about two-thirds of cases. Despite surgical reattachment, the visual outcome is poor, with only about 40% of patients achieving vision of 5/200 or better. It is generally accepted that further advances will occur only when it is possible to pharmacologically modify vitreoretinal scarring.

The cells most commonly reported to comprise proliferative vitreoretinopathy membranes include fibroblasts, retinal pigment epithelial cells, and glial cells. These types of cells have been reported to adhere to ECM proteins, synthesize ECM proteins, and express cell surface receptors for ECM proteins.

There are at least three components in the progression of proliferative vitreoretinopathy which lead to retinal detachment: cell migration, proliferation, and contraction. In order to monitor each of these components, three different assay systems may be used. The systems employ cultured dermal fibroblasts: (1) Boyden microchemotaxis chambers may be used to assess cell migration, (2) direct counts of cultures of fibroblasts may be carried out to examine cell proliferation, and (3) the collagen gel shrinkage assay may be employed to assess contraction. The collagen gel shrinkage assay has also been used to analyze the mechanisms by which the cells contract and induce retinal detachment.

These in vitro systems have been used to test a number of antimetabolites as well as agents that affect the cytoskeleton, such as cytochalasin B, colchicine, and taxol. These cytoskeleton affecting agents are thought to affect all three components noted above, since cell migration, division, and contraction are all dependent on the activity of the cytoskeleton.

The activity of dermal fibroblasts in assay systems containing daunomycin, cytochalasin B, colchicine, and taxol has been examined (see Verdoorn et al, *Arch. Ophthalmol.*, 104, 1216–1219 (1986)). Colchicine was found to be most effective at inhibiting gel contraction followed by taxol and cytochalasin B. Daunomycin was not found to inhibit contraction. All four drugs inhibited cell proliferation, with daunomycin and taxol being the most effective. Migration was most inhibited by daunomycin, followed by colchicine and taxol. Cytochalasin B had a minimal effect on cell migration. Taxol has been tested in the gel contraction model and shown to inhibit cell migration, proliferation, and contraction.

Animal Models of Proliferative Vitreoretinopathy

Rabbit models of proliferative vitreoretinopathy have been developed and are widely accepted as reasonable representations of the human clinical disease process. In particular, the rabbit model, reported in Chandler et al., *Graefe's Arch. Clin. Exp. Ophthalmol.*, 224, 86–91 (1986) and Thresher et al., *Graefe's Arch. Clin. Exp. Ophthalmol.*, 221, 192–198 (1984), is widely used. This model has been used to test a variety of agents for their ability to inhibit proliferative vitreoretinopathy and vitreoretinal scarring.

Prior experimental therapies have tested the effectiveness of a variety of toxic antimetabolites such as 5-fluorouracil, methotrexate, adriamycin, vincristine, mitomycin, cisplatin, bleomycin, cytocine arabinoside, daunomycin, retinol, colchicine, and aclacinomycin A to control the proliferation of the cells. Taxol reduces traction retinal detachment induced by injected chorioretinal fibroblasts following 0.5 μg intravitreal injection. However, none of these compounds has come into common clinical use in part due to concerns over retinal toxicity.

Intraocular corticosteroid therapy as a potential treatment for proliferative vitreoretinopathy has also been investigated in a rabbit model. The incidence of retinal detachment was reduced from 93% to 75% when eyes were injected with triamcinolone acetonide. The proliferation of injected fibroblasts was reduced in treated eyes due to the steroid mediated inhibition of mitosis. Subsequent experiments, however, showed that intraocular steroids were unable to inhibit the contraction of epiretinal membranes.

Heparin, a glycosaminoglycan, has been shown to inhibit fibroblast-mediated contraction of type I collagen gels. In addition, heparin inhibits the proliferation of human scleral fibroblasts and retinal pigmented epithelial cells and has been shown to prevent the development of intraocular fibrin membranes in the standardized proliferative vitreoretinopathy rabbit model. In the studies in the rabbit model, however, increased postoperative bleeding was observed.

A synthetic peptide, RGDS (Arg-Gly-Asp-Ser) (SEQ ID NO:16) originally derived from the extracellular matrix protein fibronectin (described below) is known to be important in mediating cell adhesion. Studies have shown that this peptide can inhibit the adhesion of retinal pigmented epithelial cells to fibronectin, type I collagen, type II collagen, and lens capsule basement membrane (see Avery et al., *Arch. Ophthalmol.*, 104, 1220–1222 (1986)). There is no indication that this peptide will act as an inhibitor of collagen gel contraction or in vivo experimental proliferative vitreoretinopathy.

In view of the current state of treatments available for retinal reattachment in patients experiencing severe proliferative vitreoretinopathy, there is a continuing need for pharmacological therapies which will suppress vitreoretinal scarring. In addition to effectively suppressing proliferative vitreoretinopathy, such a pharmacological therapy should avoid cytotoxicity or other significant side effects.

Glaucoma

Glaucoma is a condition characterized by increased intraocular pressure in the eye which, if left untreated, leads to blindness. The increase in the intraocular pressure can be initially treated with medications but eventually may need surgery to lower the pressure in the eye to prevent blindness. The common surgery performed is filtration surgery. This surgery lowers the intraocular pressure by creating an alternate outflow channel that allows the egress of aqueous humor (the fluid within the eye) from the inside of the eye to the subconjunctival space (under the surface covering of the eye). Failure of glaucoma filtration surgery may result in increasing intraocular pressure. The most common cause of failure of glaucoma filtration surgery is scarring. The scarring is typically caused by the proliferation of cells (fibroblasts) and fibrosis in the subconjunctival space. Scarring can lead to an increase in intraocular pressure. To inhibit this process, several agents including anti-neoplastic agents (cancer chemotherapy) and corticosteroids have been studied experimentally, both in vivo and in vitro.

Many pharmacologic agents, including mitomycin-C and 5-fluorouracil, have been used to modulate the wound healing which follows filtration surgery. Filtration surgery is most likely to fail in eyes that have undergone previous cataract or glaucoma surgery. Youth, African-American ancestry, and active inflammation in the eye are also associated with increased risk of failure of the filtration surgery. Mitomycin-C and 5-fluorouracil are commonly used under these conditions to improve the success of the filtration surgery. 5-Fluorouracil has the drawback of frequent postoperative injections and is associated with complications such as wound leakage and corneal epithelial defects. Mitomycin-C is convenient in that it only needs a single application at the time of surgery but it may cause excessive filtration and results in persistent low eye pressure and its associated problems including decreased vision. There is accordingly a demand for other therapies which will inhibit scarring and increase the success rate of filtration surgery, while avoiding the complications seen with 5-fluorouracil and mitomycin-C.

Animal Models of Glaucoma Filtration Surgery

Rabbit models of glaucoma filtration surgery have been developed and are widely accepted as models of human glaucoma filtration surgery. In particular, the rabbit model described by Bergstrom et al., in *Arch. Ophthalmology*, 109(12), 1725–1730 (1991), is widely used. This model has been used to test a variety of agents for their ability to inhibit scarring after glaucoma filtration surgery.

The rabbit provides an excellent model to study filtration bleb failure because the rabbit exhibits a prolific fibroblastic response after surgery. Typically, the scarring and fibroblast proliferation results in failure of the surgery in untreated rabbits in only 9–14 days due to an inhibition or blocking of fluid drainage with a resulting increase in intraocular pressure. The fibroblast proliferation observed after filtration surgery is similar to the vigorous recruitment of fibroblasts that occurs in proliferative vitreoretinopathy and in other insults and conditions of the rabbit eye.

The rabbit model has been used to test a variety of therapeutic agents including antimetabolites like mitomycin, bleomycin, 5-fluorouracil (5-FU), inhibitors of connective tissue formation such as β-aminopropionitrile and D-penicillamine, and other compounds such as tissue plasminogen activator and corticosteroid drugs. Most of these agents are effective but have undesirable side effects. Mitomycin and 5-FU have shown activity in the rabbit model and have allowed investigation of various routes of administration. For example, 5-FU has been administered in a collagen matrix implant or in a sponge. Concern over toxicity has limited the use of these compounds in humans, however.

In view of the current state of treatments available for failure of glaucoma filtration surgery, there is a continuing need for pharmacological therapies which will prevent scarring and fibroblast proliferation in the area of bleb formation. In addition, to effectively diminish scarring and failure in glaucoma filtration surgery, such a pharmacological therapy must avoid cytotoxicity or other significant side effects.

SUMMARY OF THE INVENTION

The present invention provides a method for treating diseases or conditions of the eye. Diseases or conditions of the eye which may be treated by the present method are typically are characterized by scarring and/or proliferation of fibroblast cells. One embodiement of the invention includes a method for treating proliferative vitreoretinopathy in an eye of a mammal. Another embodiment of the invention includes a method for treating glaucoma in an eye of a mammal. The glaucoma treatment may include improving and preventing failure of glaucoma filtration surgery.

In one embodiment of the invention the method includes administering to the eye an effective amount for suppressing vitreoretinal scarring of a polypeptide which suppresses fibroblast-mediated collagen gel contraction. In another embodiment of the invention the method includes administering to the eye for treating glaucoma an effective amount of a polypeptide that inhibits fibroblast proliferation and/or that inhibits scarring after glaucoma filtration surgery.

The polypeptide of the invention typically includes a sequence of at least about 5 amino acids corresponding to an amino acid sequence selected from the group of an amino acid sequence within the 33 kD fragment of the A chain of fibronectin, an amino acid sequence within the carboxy-terminal globular domain (G domain) of the A chain of laminin, and an amino acid sequence within the NC1 domain of the α2 chain of type IV collagen. For treating glaucoma, the polypeptide preferably includes an amino acid sequence within the NCI domain of the α2 chain of type IV collagen. However, it is envisioned that polypeptides including smaller amino acid sequences from within these domains, e.g., sequences of at least about three amino acids, may also be used. The polypeptides are at least about 5, and preferably at least about 8, amino acids in length, although smaller polypeptides may also be employed. The polypeptides may be prepared by conventional solid phase peptide synthesis or recombinant methods. The formulas of the preferred polypeptides of the invention are:

Leu-Ala-Gly-Ser-Cys-Leu-Ala-Arg-Phe-Ser-Thr-
Met (Hep-II) [SEQ ID NO:3];

Lys-Ala-Thr-Pro-Met-Leu-Lys-Met-Arg-Thr-Ser-Phe-His-Gly-Cys-
Ile-Lys (R37) [SEQ ID NO:5];

Lys-Asn-Leu-Glu-Ile-Ser-Arg-Ser-Thr-Phe-Asp-Leu-Leu-Arg-Asn-
Ser-Tyr-Gly-Val-Arg-Lys (R26) [SEQ ID NO:7];

and

Ser-Pro-Pro-Arg-Arg-Ala-Arg-Val-Thr (FN-C/H-IV [SEQ ID NO:12].

Polypeptide Hep-II formally represents isolated residues 49–60 from the NC1 domain of the α2 chain of type IV collagen. The single letter amino acid code for polypeptide Hep-II is LAGSCLARFSTM.

Polypeptide R37 formally represents isolated residues 2615–2631 from the G domain of the A chain of laminin. The single letter amino acid code for polypeptide R37 is KATPMLKMRTSFHGCIK.

Polypeptide R26 formally represents isolated residues 2443–2463 from the G domain of the A chain of laminin. The single letter amino acid code for polypeptide R26 is KNLEISRSTFDLLRNSYGVRK.

Polypeptide FN-C/H-IV formally represents residues 1784–1792 from the 33 kD fragment of the A chain of fibronectin. The single letter amino acid code for polypeptide FN-C/H-IV is SPPRRARVT.

Of these four polypeptides, polypeptides Hep-II and R37 are most preferred.

Another embodiment of the present invention provides a method for treating diseases and conditions of the eye that include scarring and/or proliferation of fibroblasts. The method includes the administration to the eye of an effective amount of a polypeptide/carrier molecule conjugate. When the disease of the eye is proliferative vitroretinopathy, each carrier molecule is preferably bound to at least one polypeptide which includes an amino acid sequence selected from the group of sequences having the formula:

Leu-Ala-Gly-Ser-Cys-Leu-Ala-Arg-Phe-Ser-Thr-
Met [SEQ ID NO:3],

Lys-Ala-Thr-Pro-Met-Leu-Lys-Met-Arg-Thr-Ser-Phe-His-Gly-Cys-
Ile-Lys [SEQ ID NO:5],

Lys-Asn-Leu-Glu-Ile-Ser-Arg-Ser-Thr-Phe-Asp-Leu-Leu-Arg-Asn-
Ser-Tyr-Gly-Val-Arg-Lys [SEQ ID NO: 7], and Ser-Pro-Pro-Arg-Arg-Ala-Arg-Val-Thr [SEQ ID NO: 12].

When the condition of the eye is glaucoma, each carrier molecule is preferably bound to a polypeptide including an amino acid sequence having the formula: Leu-Ala-Gly-Ser-Cys-Leu-Ala-Arg-Phe-Ser-Thr-Met [SEQ ID NO:3]. In a preferred embodiment, the carrier molecule includes a biological carrier molecule such as albumin or a synthetic carrier molecule such as methylcellulose.

BRIEF DESCRIPTION OF THE DRAWINGS

FIG. 27 is a graph showing the effect of the peptide Hep-II on intraocular pressures after glaucoma filtration surgery. In addition to varying the concentrations of Hep-II, albumin and distilled water were included as negative controls.

DETAILED DESCRIPTION OF THE INVENTION

Figure 1:
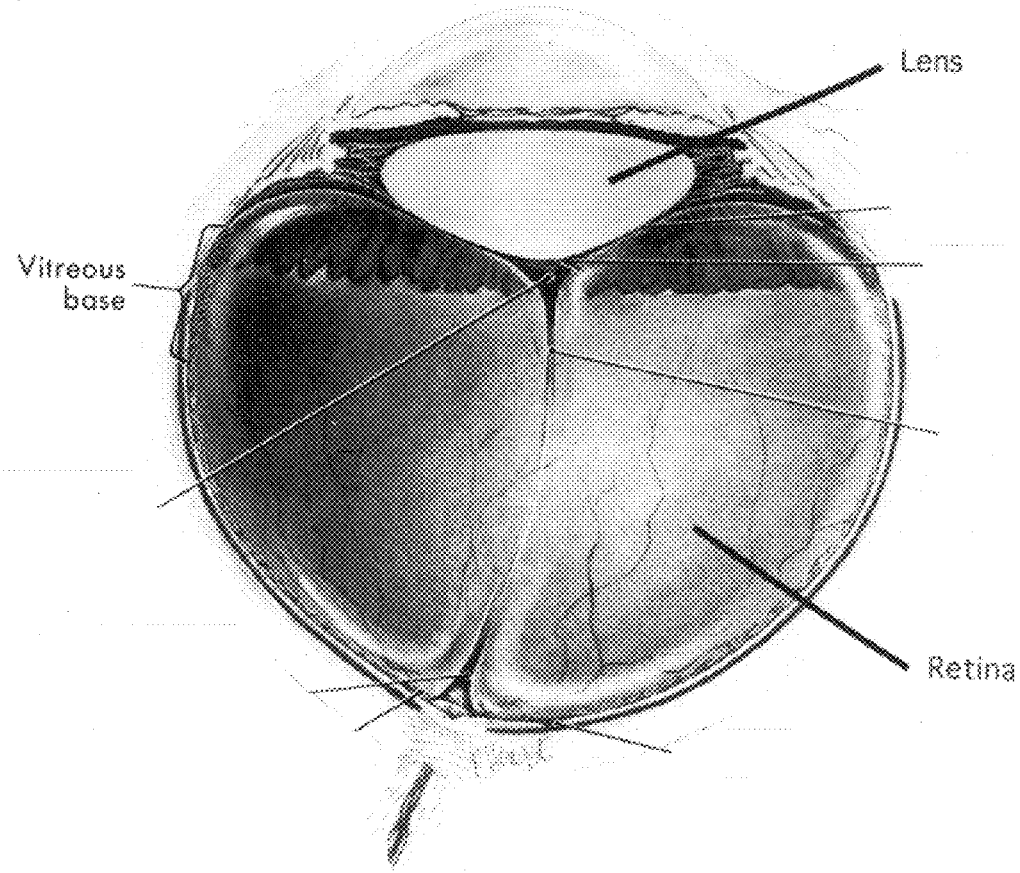
FIG. 1 depicts a cross sectional schematic anatomical diagram of a normal eye, demonstrating attached retina.
Figure 2:
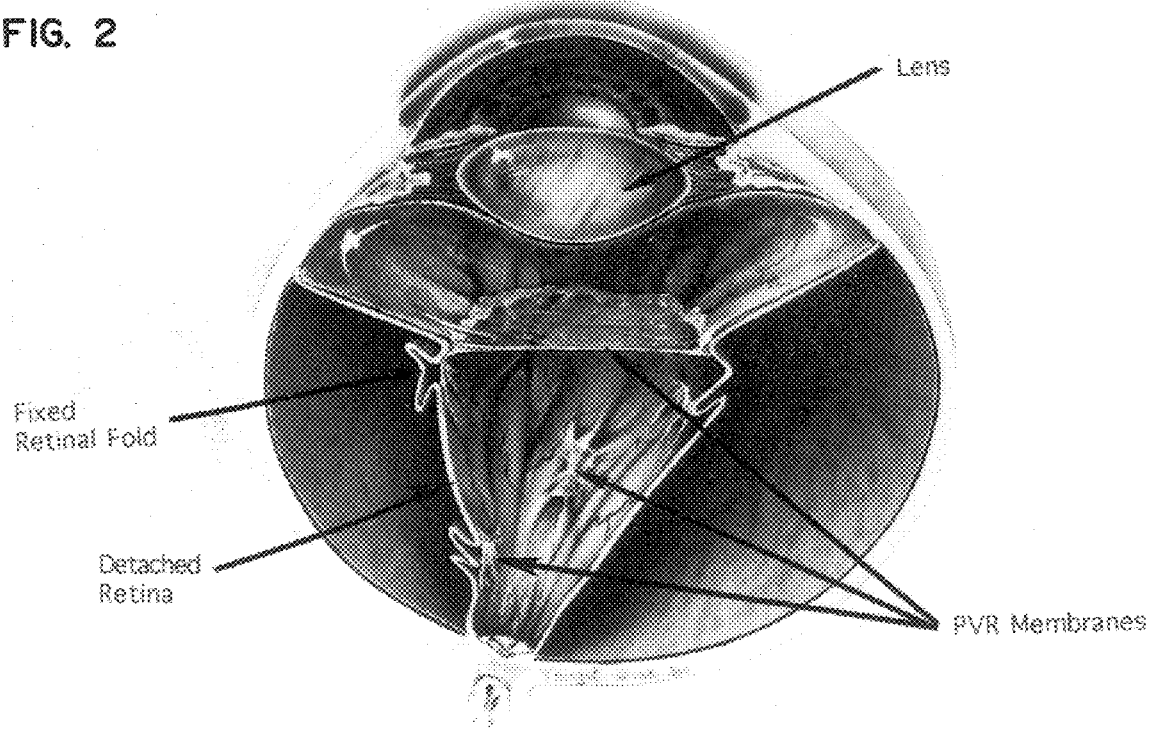
FIG. 2 depicts a cross sectional schematic anatomical diagram of an eye with total retinal detachment secondary to proliferative vitreoretinopathy. Epiretinal membranes can be seen on the surface over fixed retinal folds, and across the mouth (opening) of the open funnel configuration retinal detachment.

Basement membranes (BMs) are thin extracellular matrices that surround epithelial tissues, blood vessels, nerves, fat cells, and smooth, striated, and cardiac muscle. These membranes are responsible for proper maintenance and compartmentalization of tissue architecture. Their status modulates repair after injury by providing the scaffolding that maintains normal tissue form during regeneration and growth. In addition, basement membranes may provide anchorage for adjacent cells and thus maintain the adjacent cells polarized and differentiated state. Furthermore, basement membranes regulate cell migration and invasion and serve as selective barriers in the filtration of macromolecules in capillaries and glomeruli. There are also indications from various systems that basement membrane molecules modify the growth and phenotype of both normal and malignant cells.

In the choroid, Bruch's membrane is a laminated membrane composed primarily of the basement membrane of the retinal pigment epithelial cells and an external layer of "elastin" fibers. In addition, there is an intermittent contribution (particularly in the macular region) by the basement membrane of the vascular choriocapillaries of the choroid. The internal limiting membrane of the retina is the second prominent basement membrane. This homogeneous membrane is secreted by the foot plates of the Muller cells and serves as the internal structural boundary of the retina, and in focal areas, the site of attachment of the cortical vitreous.

Basement membrane/extracellular matrix components, in particular laminin, type IV collagen, and fibronectin, are important in the phenotypic modulation of a variety of cells. These three proteins are relatively large, complex modular molecules, each having multiple subunits. Each protein has several domains or modules with functional properties ascribed to them, including: domains that promote cell adhesion, spreading, and/or migration; domains that promote neurite extension from neurons and neuronal tumor cell lines; domains that bind glycosaminoglycans, such as heparin; and domains that bind integrins. Some of these domains may have multiple functions. These functional domains have been localized by a variety of techniques, including: digestion of the proteins with proteolytic enzymes followed by purification of fragments, the use of antibodies (ABs) against specific domains to inhibit functional activity, chemical synthesis of peptides from functionally active domains, production of recombinant polypeptides, and site-directed mutagenesis studies. In addition, these three proteins potentiate the adhesion, spreading, migration, and invasiveness of a variety of cell types. The proteins can also modify the in vitro growth, morphology, survival, and differentiation of various cells.

Early immunofluorescence studies with normal mouse tissues demonstrated that in a cross-section of the posterior part of a mouse eye, laminin is localized to the basement membrane zone of Bruch's membrane, the basement membrane of choroid vessels and retinal vessels, and the epithelial basement membrane of the sclera (see Foidart et al. *Lab. Invest.*, 42, 336–342 (1980)). In other studies, immunohistochemical staining of isolated retinal vessels from rats indicated that laminin was localized along the retinal vessel walls (see Gordon et al., *Cell Tissue Res.*, 244, 583–589 (1986)). In another type of study, antibodies against laminin or type IV collagen were injected into the eyes of quail embryos and the eyes were analyzed 20 hours later. Laminin and type IV collagen were predominantly localized in the optic fiber layer, as well as a patchy distribution on the surface of axons and the endfeet of ventricular (neuroepithelial) cells (see Halfter et al., *Cell Tissue Res.*, 249, 487–496 (1987)). These results suggest that laminin may play a critical role in axon extension in the retina during early development of the optic fiber layer. In addition, it has been demonstrated that laminin and fibronectin promote the migration of Schwann cells, as well as the outgrowth of neurites from neurons (see Haugen et al., *J. Cell Biol.*, 111, 2733–2745 (1990) and McCarthy et al., *J. Cell Biol.*, 97, 772–777 (1983)). Further studies have shown that Schwannoma cells and the developing optic nerve in rats produce laminin and/or fibronectin (see McLoon et al., *J. Neurosci.*, 8, 1981–1990 (1988) and Palm et al., *J. Cell Biol.*, 96, 1218–1226 (1983)).

For the purposes of the invention, polypeptides corresponding substantially to an amino acid sequence from within the ECM proteins, laminin, fibronectin and collagen, are defined to include polypeptides which correspond to sequences within allelic variants as well as mutants (e.g., substitition, deletion or addition mutants). The polypeptides maintain the functional activity of the ECM to interact with cells, such as fibroblast cells, epithelial cells or glial cells, and possess a high degree of sequence homology with the natural protein. Preferably, polypeptides corresponding substantially to ECM sequences have at least about 70% and more preferably at least about 90% sequence homology with the native sequence. Typically, substitution mutations will include conservative amino acid substitutions such as alanine for glycine, phenylalanine for tyrosine, serine for threonine, alanine for serine, aspartate for glutamate, lysine for arginine, valine for leucine, and the like.

Laminin Synthetic Polypeptides

Figure 3:
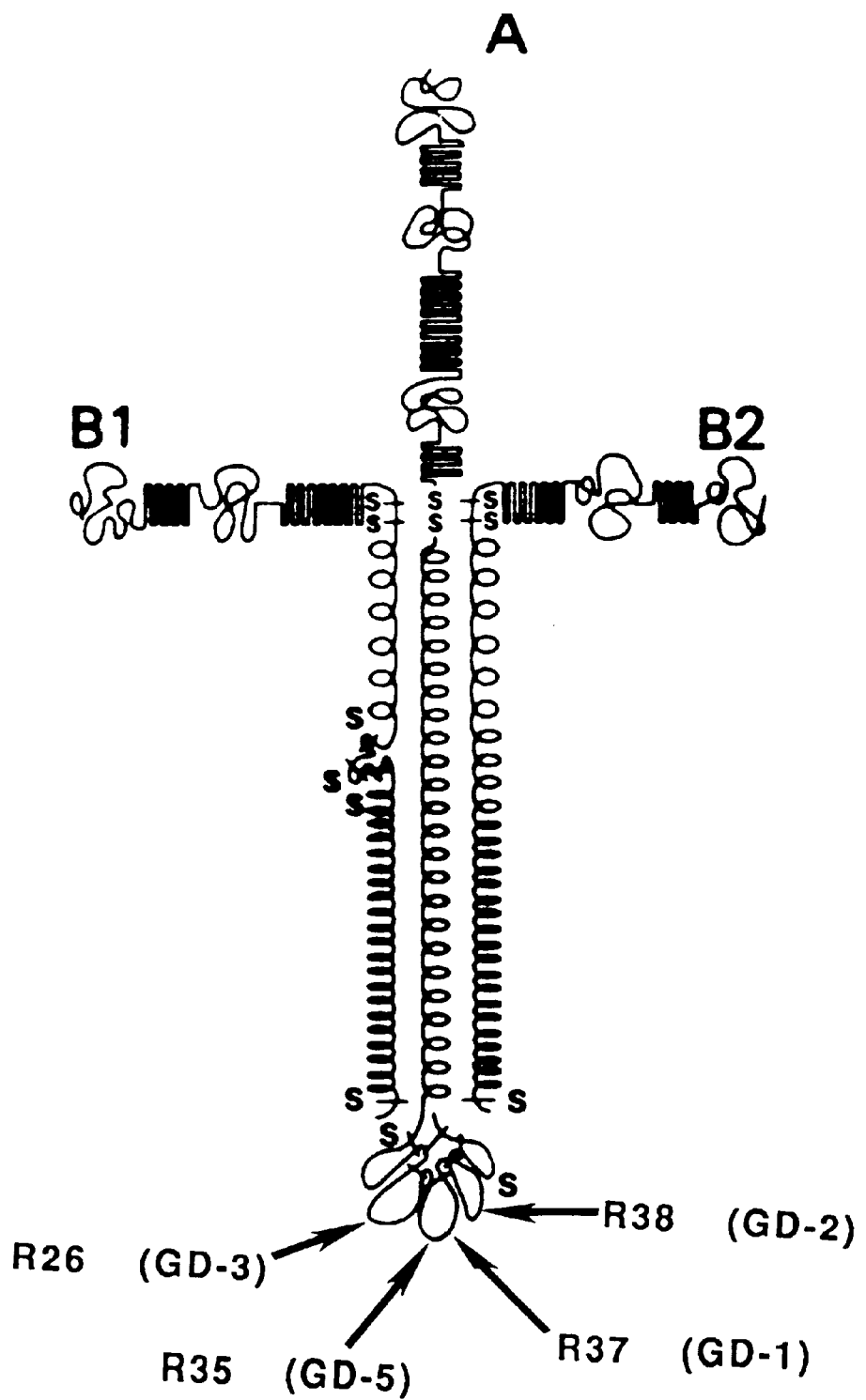
FIG. 3 is a diagrammatic representation of the entire laminin molecule with showing the A, B1 and B2 chains. The locations of the laminin peptides employed in this study are shown within the carboxy terminal globular domain (G domain) of the A chain at the distal end of the long arm.

Laminin, an 850 kD glycoprotein, is the major noncollagenous protein of basement membranes and is readily isolated from the murine Engelbreth-Holm-Swarm (EHS) tumor. Laminin from the EHS source has a cruciform appearance by rotary shadowing techniques, with two globular domains on the ends of the lateral short arms, three globular domains at the end of the proximal short arm, and one globular domain at the end of the long arm (FIG. 3). The EHS-derived laminin is composed of three chains (A=400 kD; B1=222 kD; B2=210 kD). The amino acid sequences for each chain of both human and mouse laminin have been predicted by sequencing cDNA clones (see Sasaki et al., *J. Biol. Chem.*, 263, 16536–16544 (1988)).

Several regions of laminin have had functional properties ascribed to them. Various cell types bind to different domains of laminin. Some cells bind near the cross-region, while others bind at the carboxy terminal globular domain (G domain) at the distal end of the long arm or to the amino terminal globular domain at the top of the A chain, and yet other cells bind to the region directly above the G domain. Using monoclonal antibodies (MABs) that inhibit tumor cell adhesion to laminin, a melanoma cell adhesion promoting domain has been localized to the long arm of laminin, directly below the intersection of the cross. Laminin also has a domain that promotes neurite extension from neurons, and domains that promote laminin self-assembly into aggregates. Other functional domains of laminin include the type IV collagen binding domains on the outer globules of the lateral short arms and the globule at the end of the long arm. Nidogen/entactin, another basement membrane glycoprotein, binds to the lateral short arm of the B2 chain near the intersection of the cross. Several heparin-binding domains of laminin have been localized by using heparin-affinity chromatography, a solid-phase radioligand binding assay, and MABs against laminin. The three heparin binding domains are located at: the carboxy-terminal globular domain of the A chain (G domain), the inner lateral short arms of the B chain(s), and directly below the intersection of the cross.

A number of polypeptides from the carboxy terminal globular domain of the A chain of laminin (FIG. 3; Table I) that promote the adhesion of a variety of cells and the outgrowth of neurites from neurons have been reported. Two of the polypeptides, R37 and R38, bind $^3$H-heparin, suggesting that cell surface glycosaminoglycans or proteoglycans may play a role in mediating cell adhesion to these two polypeptides. In contrast, polypeptides R26 and R35 do not bind $^3$H-heparin. However, HT-1080 human fibrosarcoma cell adhesion to polypeptide R26 can be inhibited by a MAB against the β1 integrin subunit, suggesting that β1 integrins play a role in mediating cell adhesion to this polypeptide.

Type IV Collagen Synthetic Polypeptides

Figure 4:
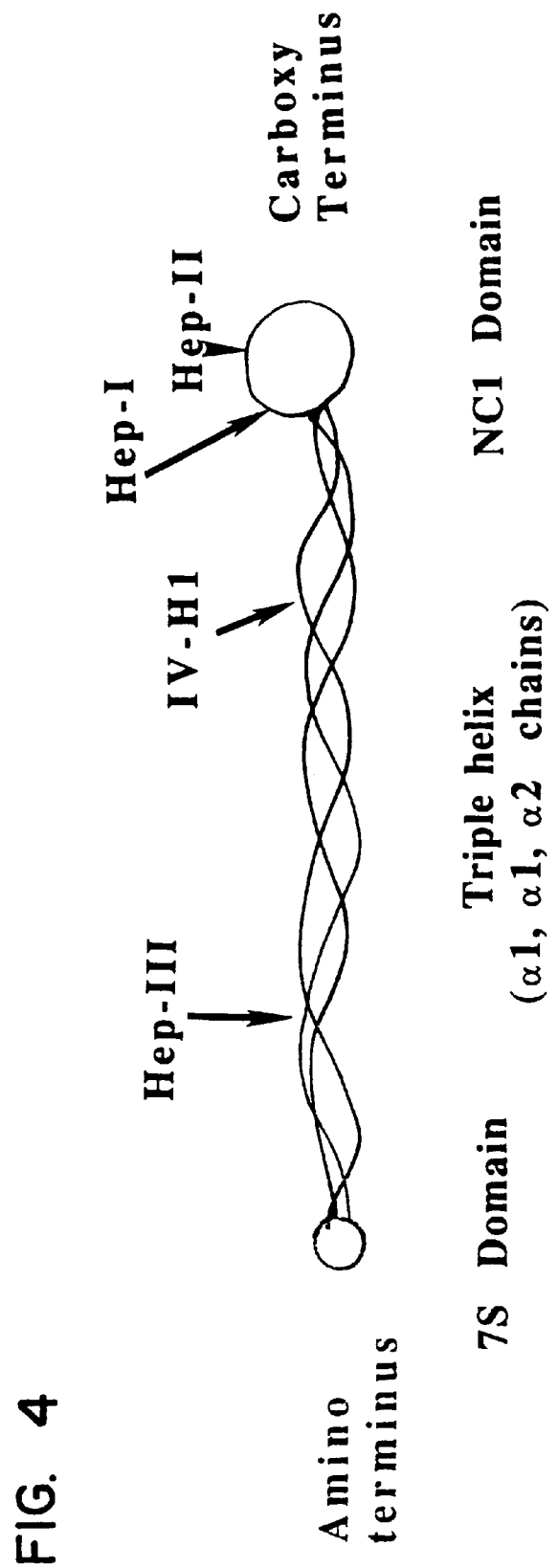
FIG. 4 is a diagrammatic representation of type IV collagen, indicating the structure of the α1(IV) and α2(IV) chains, each with a major non-collagenous, NC1 domain and the triple helix-rich domain and depicting the location of the type IV collagen polypeptides studied.

Type IV collagen, as produced by the EHS tumor, is a ~500 kD protein composed of three chains [two α1(IV)=185 kD and one α2(IV)=170 kD] (FIG. 4). A single heterotrimer (monomer) contains a globular, noncollagenous domain, termed NC1, at one end and a long (420 nm) helical segment containing several nonhelical disruptions (see Timpl et al., *Eur. J. Biochem.*, 20, 203–211 (1986)). Monomers of type IV collagen associate both by way of their NC1 domains and their amino-terminal 7S domains to form the characteristic chicken wire-like structure that serves as the scaffold of basement membranes.

Many functional properties have been ascribed to domains of type IV collagen. Both the NC1 domain and the major triple helical fragment of type IV collagen promote the adhesion of murine melanoma cells, yet only the helical fragment promotes murine melanoma cell migration. Normal human keratinocytes have also been shown to adhere to the triple helical fragment. Two sites on type IV collagen have been shown to preferentially bind laminin: one at ~25 to 35% of the length of the molecule as measured from the NC1 domain and the other at a site close to the amino terminus. In addition, three sites on type IV collagen have been reported to specifically bind heparin: the NC1 domain, and 100 and 300 nm from the NC1 domain.

Several chemically synthesized polypeptides derived from type IV collagen have been described that have functional activity (FIG. 4; Table I). Polypeptide Hep-I from the α1(NC1) chain, polypeptide Hep-II from the NC1 domain of the α2 chain, and polypeptide Hep-III from an interruption of the triple helical sequence of the α1(IV) chain, have been reported to bind heparin. More recently, polypeptide Hep-I has been shown to promote the adhesion and spreading of bovine aortic endothelial cells while polypeptide Hep-III has been shown to promote the adhesion of normal human keratinocytes. Another polypeptide, termed IV-H1, is derived from a continuous collagenous region of the major triple helical domain of the human α1(IV) chain. Polypeptide IV-H1 promotes the adhesion, spreading, and motility of a variety of cell types of disparate histological origins.

Fibronectin Synthetic Polypeptides

Figure 5:
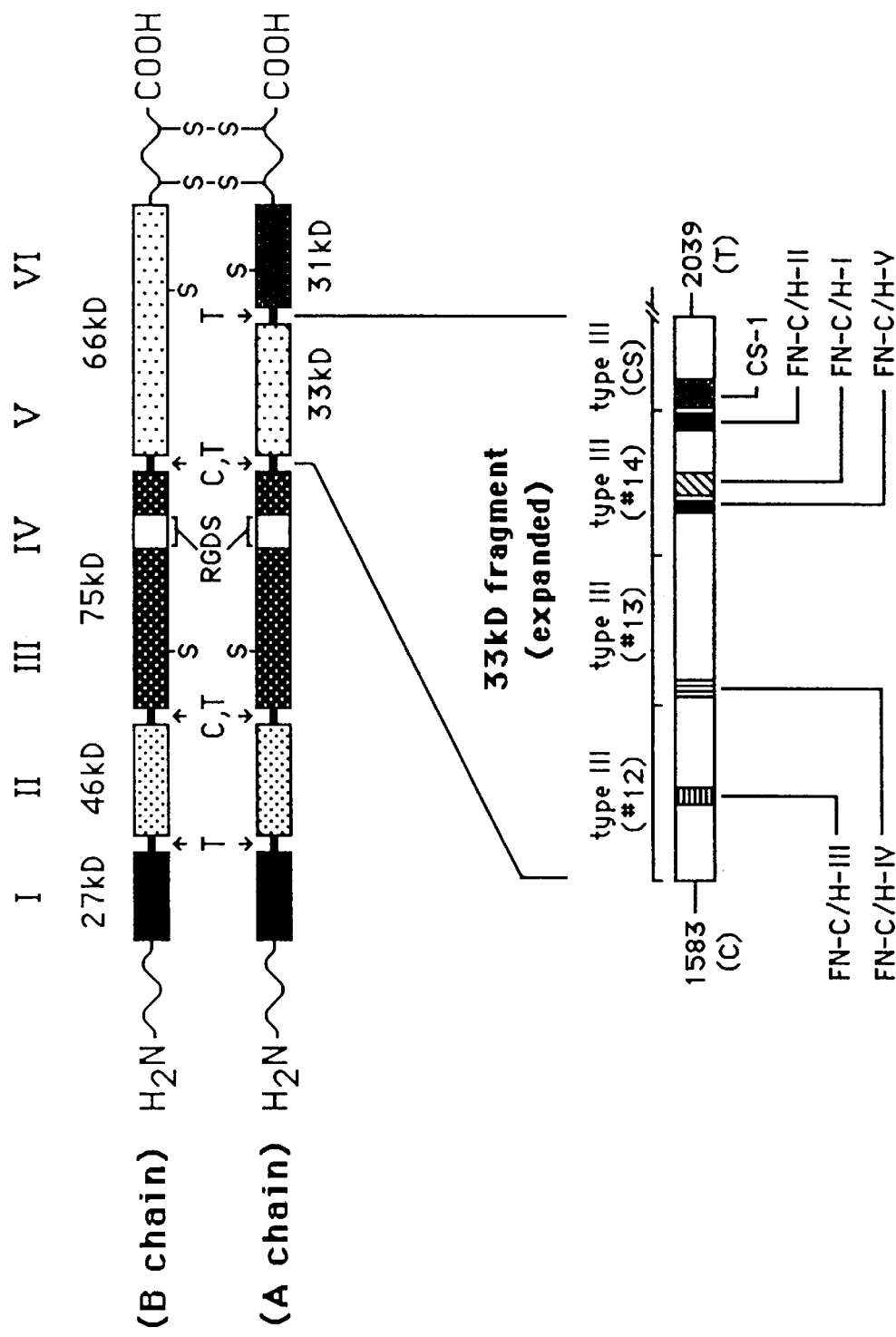
FIG. 5 is a diagrammatic representation of fibronectin showing the location of a number of the polypeptides studied on the 33 kD fragment (domain V) of the A chain of fibronectin.

Fibronectin is widely distributed in tissues throughout the body in an insoluble form and is present in plasma and most other bodily fluids in a soluble form. Fibronectin, a ~440 kD glycoprotein isolated from human plasma is composed of two chains (A and B=210–250 kD) (FIG. 5). Fibronectin exists in several variant forms that differ in sequence at three general regions of alternative splicing of its precursor mRNA; resulting in about 20 different forms of human fibronectin subunits.

The structure of fibronectin has been previously described in U.S. Pat. Nos. 4,839,464 and 5,019,646, the disclosures of which are incorporated by reference herein. The A chain digest contains a 11.5 kD RGDS-mediated cell adhesion fragment (domain IV), a 33 kD fragment (domain V) and a 31 kD fragment (domain VI). The polypeptides useful for the present invention correspond to isolated regions of domain V. Domain V represents isolated amino acid residues 1583–2039 of the A chain of fibronectin.

A variety of different functional activities have been assigned to domains of fibronectin. Starting at the amino terminal end of fibronectin, the 27 kD fragment binds heparin weakly and binds Staphylococcus and fibrin; the 46 kD fragment binds collagen; the 75 kD fragment promotes cell adhesion and migration; and the 33 kD fragment (domain V) binds heparin and promotes cell adhesion and cell spreading. The wide spectrum of activities attributed to the various domains of fibronectin enable this extracellular matrix molecule to perform a multitude of functions. For example, fibronectin plays an important role in clot formation, wound repair, epithelialization, inflammation, and host defense.

A variety of polypeptides from the functionally active domains of fibronectin have been chemically synthesized. The peptide sequence RGD from the 75 kD fragment was the first synthetic polypeptide from a BM/ECM protein shown to have cell adhesion activity. The sequence RGD has been found in other BM/ECM molecules and cell surface integrins adhere to this peptide sequence. The 33 kD fragment of fibronectin contains a number of sequences that promote cell adhesion (FIG. 5; Table I). Polypeptide CS1 promotes cell adhesion, cell spreading, and neurite extension by dorsal root ganglion neurons, through an integrin-dependent mechanism. Polypeptides FN-C/H-I, II, III, IV, and V are known to bind $^3$H-heparin, promote the adhesion, spreading, and/or migration of a variety of cell types, and promote neurite outgrowth.

Synthesis of Polypeptides

The polypeptides used in the invention were synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill. (2d ed., 1984), the disclosure of which is incorporated by reference herein. This method of synthesis is understood to be illustrative only and not intended to limit the scope of the present invention in any way.

The Merrifield system of peptide synthesis uses a 1% cross-linked polystyrene resin functionalized with benzyl chloride groups. The halogens, when reacted with the salt of a protected amino acid, will form an ester, linking it covalently to the resin. The benzyloxy-carbonyl (BOC) group is used to protect the free amino group of the amino acid. This protecting group is removed with 25% trifluoroacetic acid (TCA) in dichloromethane (DCM). The newly exposed amino group is converted to the free base by 10% triethylamine (TEA) in DCM. The next BOC-protected amino acid is then coupled to the free amine of the previous amino acid by the use of dicyclohexylcarbodiimide (DCC). Side chain functional groups of the amino acids are protected during synthesis by TFA stable benzyl derivatives. All of these peptides of the present invention were synthesized at a University of Minnesota microchemical facility by the use of a Beckman System 990 peptide synthesizer or Applied Biosystems synthesizer. The polypeptides may also be synthesized using the fluorenylmethoxycarbonyl (FMOC) group to protect the free amino group of the amino acid.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0 M acetic acid, followed by lyophilization of the extract.

Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptides is by amino acid analysis. The polypeptides are first hydrolyzed anaerobically for 24 hours at 110° C. in 6 M HCl (constant boiling) or in 4 N methane sulfonic acid, when cysteine or tryptophan are present. The hydrolyzed amino acids are separated by ion exchange chromatography using citrate buffers. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981). Peptides could also be modified by amidation or various other means.

The present invention provides a method for treating proliferative vitreoretinopathy in an eye of a mammal. The method includes administering to the eye for suppressing vitreoretinal scarring an effective amount of a polypeptide which suppresses fibroblast-mediated collagen gel contraction. The polypeptide may be in free form or may be covalently bound to a carrier molecule as part of a polypeptide/carrier molecule conjugate. In a preferred embodiment, the polypeptide suppresses the proliferation within the eye of at least one of fibroblast cells, retinal pigmented epithelial cells, or glial cells. In another preferred embodiment, the present polypeptides suppress the contraction of epiretinal membranes. Preferred polypeptides of the invention may suppress the migration within the eye of at least one of fibroblast cells, retinal pigmented epithelial cells or glial cells and/or inhibit the attachment of these cells to the extracellular matrix on the retinal surface. The use of the present method is particularly advantageous where the mammal is a human.

Polypeptide Carrier Conjugates

Polypeptides synthesized can be employed in the present invention in a monovalent state (i.e., free polypeptide or single polypeptide fragment coupled to a carrier molecule such as a biological carrier molecule, including collagen, a glycosaminoglycan, a proteoglycan, a lipid, albumin or the like). Conjugates formed by coupling the polypeptide or fragment to a synthetic carrier molecule, such as a polymer (e.g., polyacrylic acid or polylactic acid), may also be employed. Preferably, as described below, to treat proliferative vitreoretinopathy, conjugates of multiple polypeptide fragments bound to a carrier molecule such as albumin (e.g., ovalbumin or human serum albumin), other proteins, polyethylene glycol, methylcellulose or the like are employed. Preferably, as described below, to treat glaucoma, conjugates of multiple polypeptide fragments bound to a carrier molecule such as albumin (e.g., ovalbumin, human serum albumin), cellulose derivatives such as methylcellulose, polyacrylic acid or polylactic acid polymers, lipids, collagen or the like are employed. Such modifications may increase the apparent affinity or change the circulatory half-life. The number of polypeptide fragments associated with or bound to each carrier molecule can be varied, but from about 4 to about 8 polypeptide fragments per carrier molecule are typically obtained under standard coupling conditions.

Administration of the Polyseptides

Patient treatment using the method of the present invention involves administering therapeutic amounts of the polypeptide composition. In the context of the present invention, the terms "treat" and "therapy" and the like refer to alleviate, slow the progression, prophylaxis, attenuation or cure of existing disease. In addition, the terms "treat" and "therapy" can refer to preventing the failure or reversal of glaucoma filtration therapy or other types of eye surgery. A polypeptide composition may be formulated with conventional pharmaceutically acceptable parenteral vehicles for administration by injection. These vehicles comprise substances which are essentially nontoxic and nontherapeutic such as water, saline, Ringer's solution, dextrose solution, Hank's solution, or the like. It is to be understood that polypeptide formulations may also include small amounts of adjuvants such as buffers and preservatives to maintain isotonicity, physiological and pH stability. Typically, the polypeptide or polypeptide carrier molecule conjugate is formulated in purified form substantially free of aggregates and other protein at concentrations ranging from about 0.0001 to about 20 mg/ml, more preferably from about 0.001 to about 10 mg/ml, and most preferably from about 0.01 to about 1.0 mg/ml.

The dose of the polypeptide formulation to be administered will depend upon the patient and the patient's medical history, and the severity of the disease process. However, the dose should be sufficient to suppress the intraocular cell proliferation and the associated scarring of the patient's eye or to inhibit resulting increases in intraocular pressure. Dosages for adult humans envisioned by the present invention and considered to be therapeutically effective will range from about 0.001 to about 10 mg/eye/day and preferably from about 0.01 to about 2.0 mg/eye/day; however, lower and higher amounts may be more appropriate.

The polypeptides or polypeptide/carrier conjugates are typically administered directly to the eye, e.g. by intravitreal injection or by subconjunctival injection. The polypeptides or polypeptide/carrier conjugates may also be introduced indirectly to the eye, such as by intravenous administration to the patient. The polypeptides or polypeptide/carrier conjugates may be administered to the eye as a component of an implant. The implant may consist of a synthetic or natural polymer or other suitable material. For example, such implants may be formed from methylcellulose, collagen, collagen sponges, hyaluronic acid/hyaluronate, sponges, a bioerodible polymer, a sustained-release membrane, and the like. Typically, the implant releases a therapeutic agent through diffusion or erosion of the implant with the resulting release of the therapeutic agent over a period of days or weeks.

The invention will be further described by reference to the following detailed examples. These examples are not meant to limit the scope of the invention which has been fully set forth in the foregoing description. Variation within the concepts of the invention are apparent to those skilled in the art.

EXAMPLE 1

Synthetic Polypeptides from ECM Proteins

Polypeptides were synthesized by the Merrifield solid phase method (see discussion above). Lyophilized crude polypeptides were purified by preparative reverse phase HPLC on C-18 columns, and characterized by amino acid analysis. Sequence determination was carried out by sequential Edman degradation from the amino terminus using an automated gas-phase sequenator. The polypeptides shown in Table I were prepared according to this procedure and used in the in vitro or in vivo studies described herein.

Prior to being used in the in vitro or in vivo studies, polypeptides were sterilized by 10,000 R of gamma irradiation. Although this dose of radiation is not strictly defined as a sterilizing dose, the use of this dose to sterilize preparations for cell culture over the past 10 years has not yielded any evidence of contamination.

TABLE I

Peptides Synthesized from BM/ECM Proteins

| Peptide Name | SEQ ID NO | Amino Acid Sequence* | Sequence Numbers** |
|---|---|---|---|
| IV-H1 | 1 | GVKGDKGNPGWPGAP | 1263–1277 |
| Hep-I | 2 | TAGSCLRKFSTM | 49–60 |
| Hep-II | 3 | LAGSCLARFSTM | 49–60 |
| Hep-III | 4 | GEFYFDLRLKGDK | 531–543 |
| R37 (GD-1) | 5 | KATPMLKMRTSFHGCIK | 2615–2631 |
| R38 (GD-2) | 6 | KEGYKVRLDLNITLEFRTTSK | 2890–2910 |
| R26 (GD-3) | 7 | KNLEISRSTFDLLRNSYGVRK | 2443–2463 |
| R35 (GD-5) | 8 | TSLRKALLHAPTGSYSDGQ | 2547–2565 |
| FN-C/H-I | 9 | YEKPGSPPREVVPRPRPGV | 1906–1924 |
| FN-C/H-IIa | 10 | KNNQKSEPLIGRKKT | 1946–1960 |
| FN-C/H-III | 11 | YRVRVTPKEKTGPMKE | 1721–1736 |
| FN-C/H-IV | 12 | SPPRRARVT | 1784–1792 |
| FN-C/H-V | 13 | WQPPRARI | 1892–1899 |
| FN-RGD | 14 | ITVAYAVTGRGDSPASSKPIS | 1485–1504 |
| CS1 | 15 | DELPQLVTLPHPNLHGPEILDVPST | 1961–1985 |

*G = Glycine; A = Alanine; V = Valine; L = Leucine; I = Isoleucine; F = Phenylalanine; Y = Tyrosine; W = Tryptophan; M = Methionine; C = Cysteine; S = Serine; T = Threonine; H = Histidine; K = Lysine; R = Arginine; D = Aspartate; E = Glutamate; N = Asparagine; Q = Glutamine; P = Proline.
**Sequence numbering as assigned in U.S. Pat. No. 5,082,926 (Hep-III) for type IV collagen, in U.S. Pat. No. 5,266,328 for laminin, and in U.S. Pat. Nos. 4,839,464 and 5,019,646 for fibronectin. The sequence numbers for type IV collagen polypeptides IV-H1, Hep-I and Hep-III are from the α1 chain and for type IV collagen polypeptide Hep-II is from the α2 chain.

EXAMPLE 2

Culture of Dermal Fibroblasts

Rabbit dermal fibroblasts were obtained from explants of skin of 6–8 day old rabbits. A 2 cm$^2$ area of skin was excised after cleansing it with iodine and alcohol. The piece of skin was finely minced using a razor blade and suspended in sterile trypsin for 10 minutes. The explants were centrifuged at 1000 rpm, washed in sterile phosphate buffered saline (PBS) and placed in 25-cm$^2$ flasks containing RPMI 1640 medium supplemented with 10l fetal calf serum and antibiotics. When cells grew out, tissue pieces and medium were removed and fresh medium added. The cells were split at a 1 to 3 ratio on reaching confluence and recultured in fresh flasks.

EXAMPLE 3

In vitro Model—Collagen Gel Contraction Assay

As indicated above, proliferative vitreoretinopathy is the result of the proliferation and migration of fibroblasts, retinal pigment epithelial cells, and glial cells, and their organization into vitreous strands and epiretinal membranes. The vitreous strands and epiretinal membranes can contract, resulting in traction retinal detachment. The ability of rabbit dermal fibroblasts to cause contraction was examined in the collagen gel shrinkage model, which serves as an in vitro model of proliferative vitreoretinopathy (see Verdoon et al., *Arch. Ophthalmol.*, 104, 1216–1219 (1986)). The ability of synthetic polypeptides derived from ECM molecules to inhibit contraction in the collagen gel shrinkage model using rabbit fibroblasts was also examined.

The ability of fibroblasts to contract collagen gels was measured according to the method described below. Fibroblast assay medium was prepared as follows:

| | |
|---|---|
| 20 ml | 10X RPMI 1640 |
| 7 ml | 5.6% NaHCO$_3$ |
| 5 ml | 0.35 M NaOH |
| 44 ml | Water |
| 2 ml | 10,000 U Penicillin/10 mg Streptomycin per ml |
| 2 ml | 2% L-Glutamine/1% pyruvate/5 mM b-mercaptoethanol |
| 20 ml | Fetal calf serum |
| 100 ml | Total volume |

Figure 6:
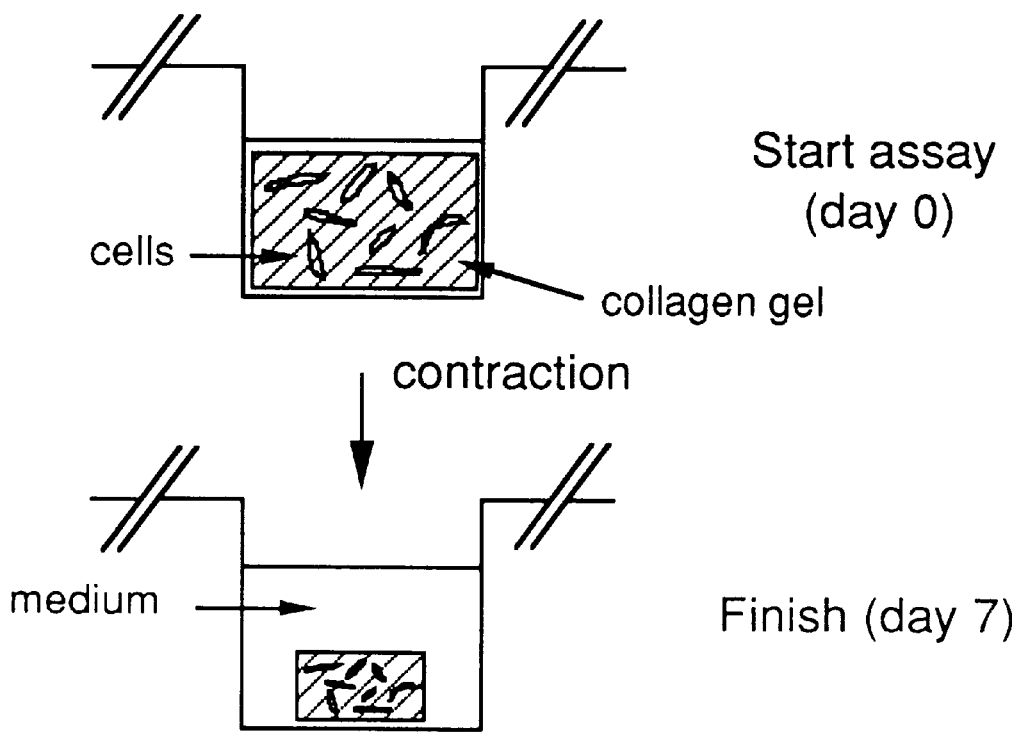
FIG. 6 is a schematic representation of the arrangement of cells, collagen gel, and tissue culture media in a well of a tissue culture plate. Cells incorporated into the Vitrogen matrix in the well form a network of interconnected strands. Within 7 days, fibroblasts incorporated into the collagen gel matrix caused the collagen gel to contract relatively uniformly.
Figure 7:
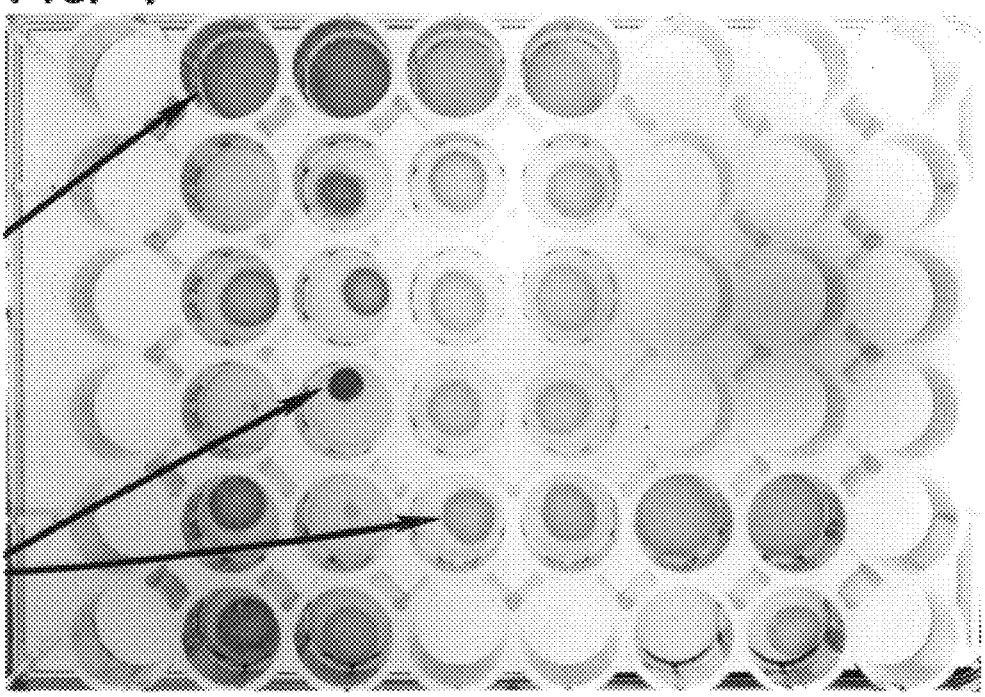
FIG. 7 shows a photograph of fibroblast-mediated collagen gel contraction in a 48-well tissue culture plate. The photograph includes representative examples of collagen gels in various stages of contraction.
Figure 8:
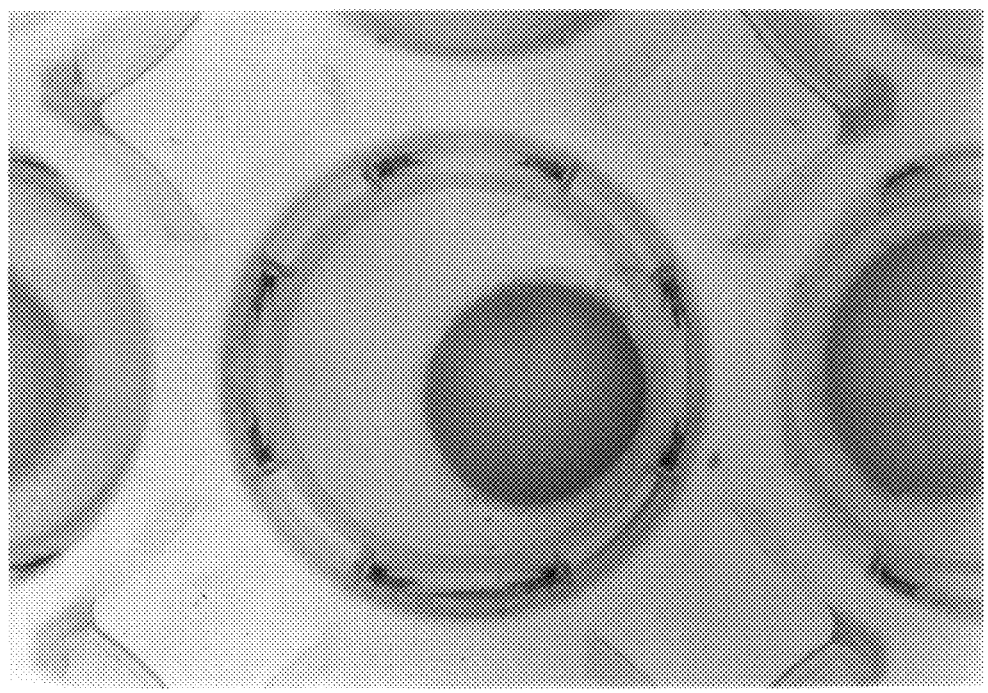
FIG. 8 is a photograph of fibroblast-mediated collagen gel contraction in a 48-well plate which shows a representative example of a collagen gel which has contracted due to the presence of fibroblasts in the gel.
Figure 9A:
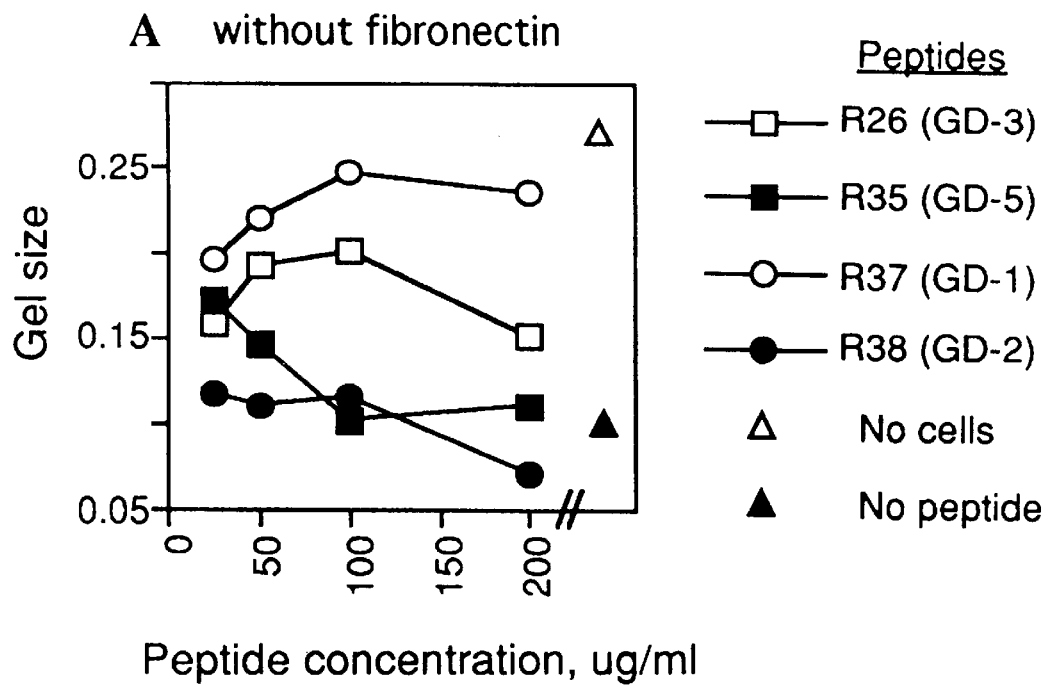
FIG. 9A is a graph showing the gel size for collagen gels, prepared in the absence of fibronectin, which were seeded with fibroblasts. Laminin-derived peptides were added to wells as indicated and after 7 days the gels were measured to determine the extent of contraction.
Figure 9B:
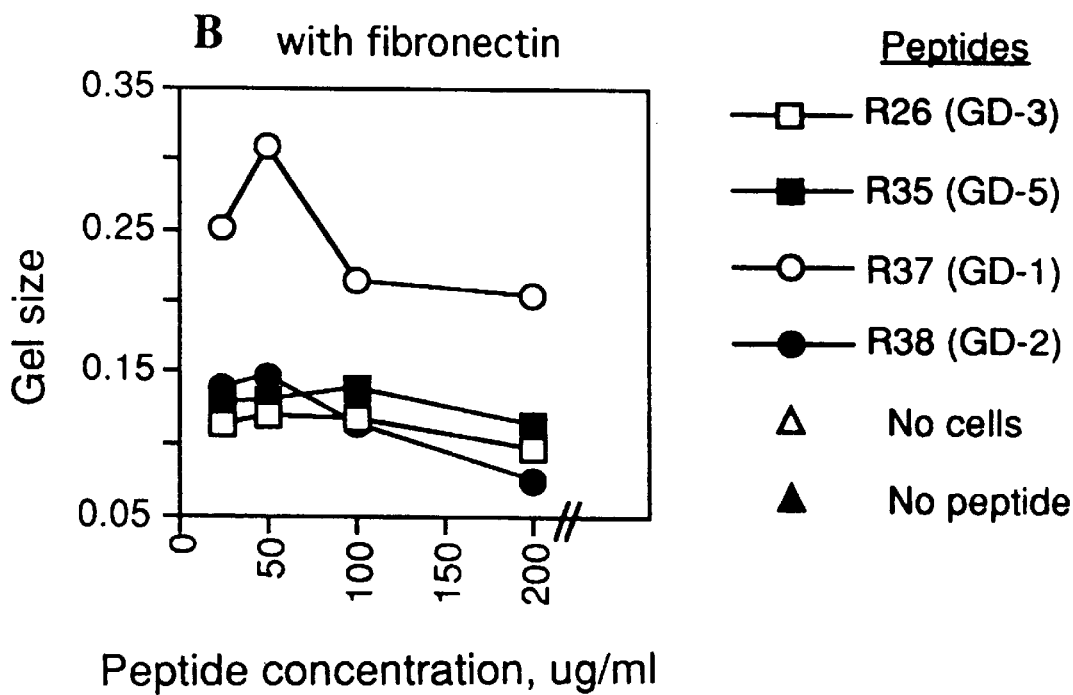
FIG. 9B is a graph showing the gel size for collagen gels, prepared in the presence of fibronectin, which were seeded with fibroblasts. Laminin-derived peptides were added to wells as indicated and after 7 days the gels were measured to determine the extent of contraction.
Figure 10A:
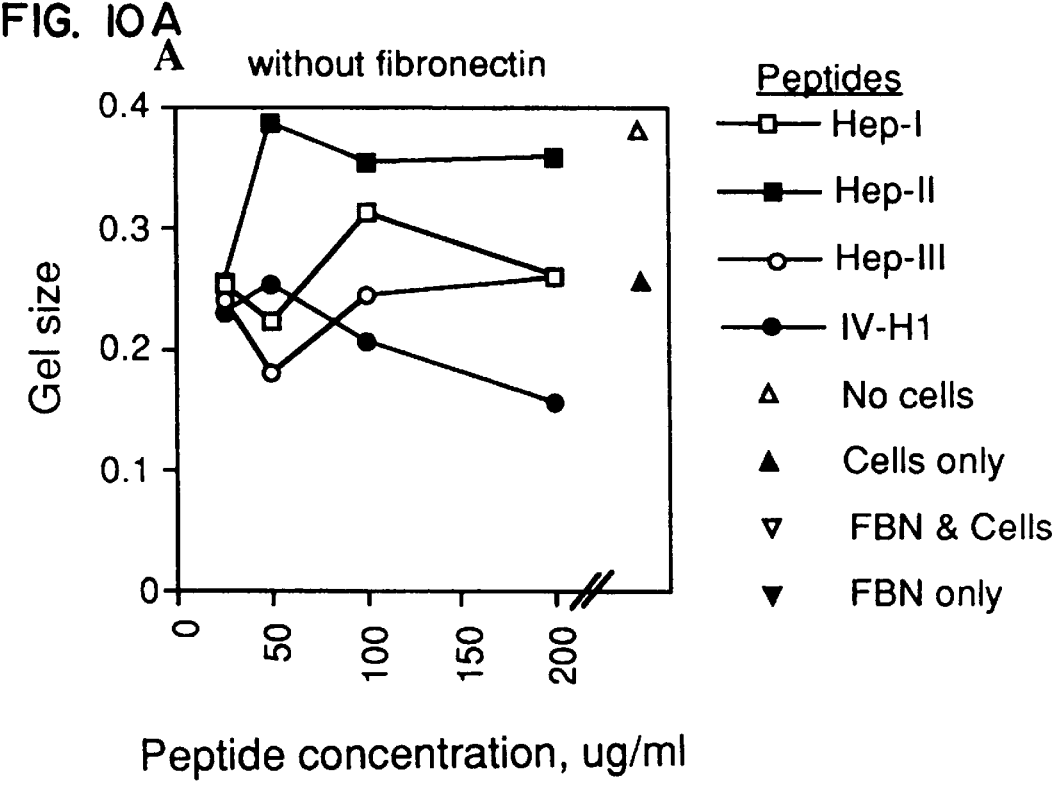
FIG. 10A is a graph showing the gel size for collagen gels, prepared in the absence of fibronectin, which were seeded with fibroblasts. Type IV collagen-derived peptides were added to wells as indicated. After 7 days, the gels were measured to determine the extent of contraction.
Figure 10B:
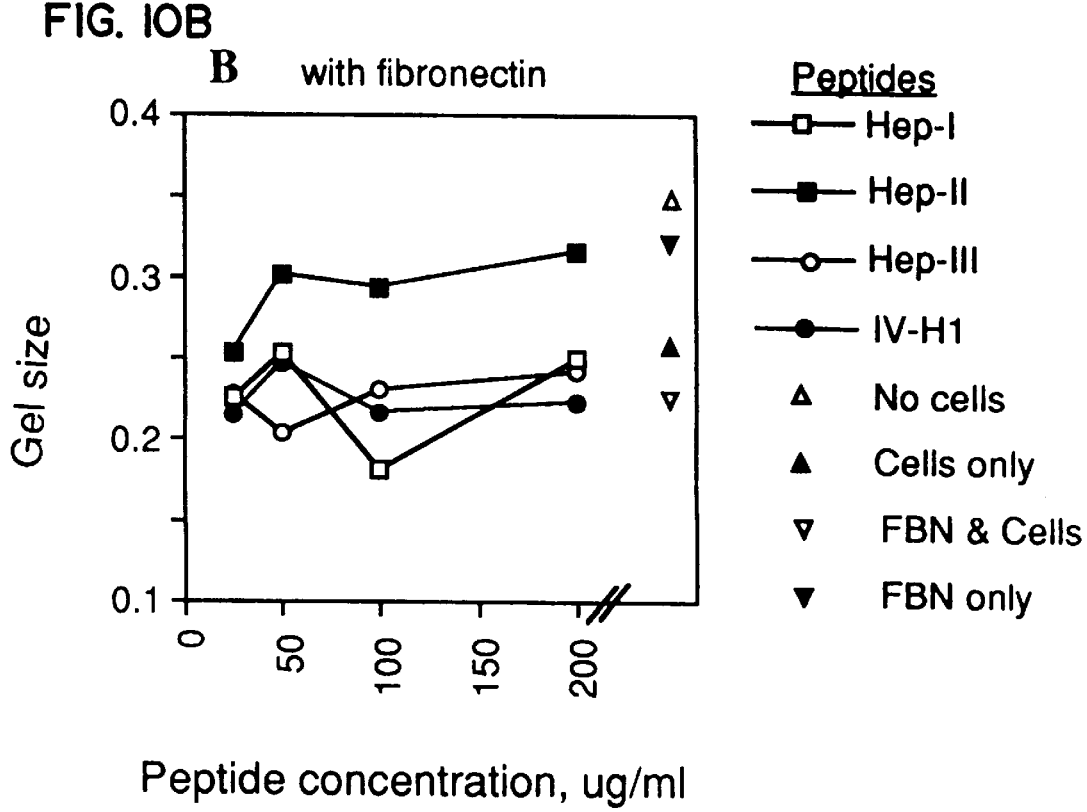
FIG. 10B is a graph showing the gel size for collagen gels, prepared in the presence of fibronectin, which were seeded with fibroblasts. Type IV collagen-derived peptides were added to wells as indicated. After 7 days, the gels were measured to determine the extent of contraction.
Figure 11A:
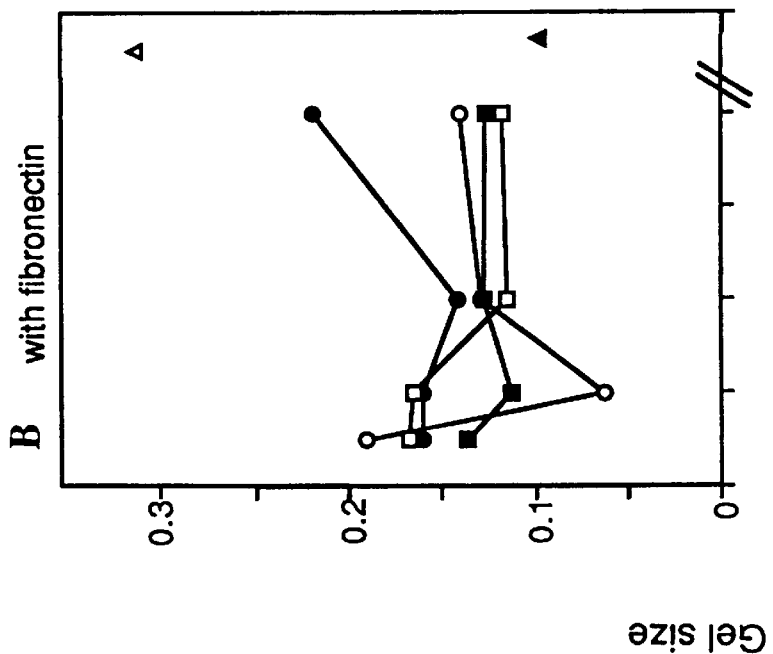
FIG. 11A is a graph showing the gel size for collagen gels, prepared in the absence of fibronectin, which were seeded with fibroblasts. Fibronectin-derived peptides were added to wells as indicated. After 7 days, the gels were measured to determine the extent of contraction.
Figure 11B:
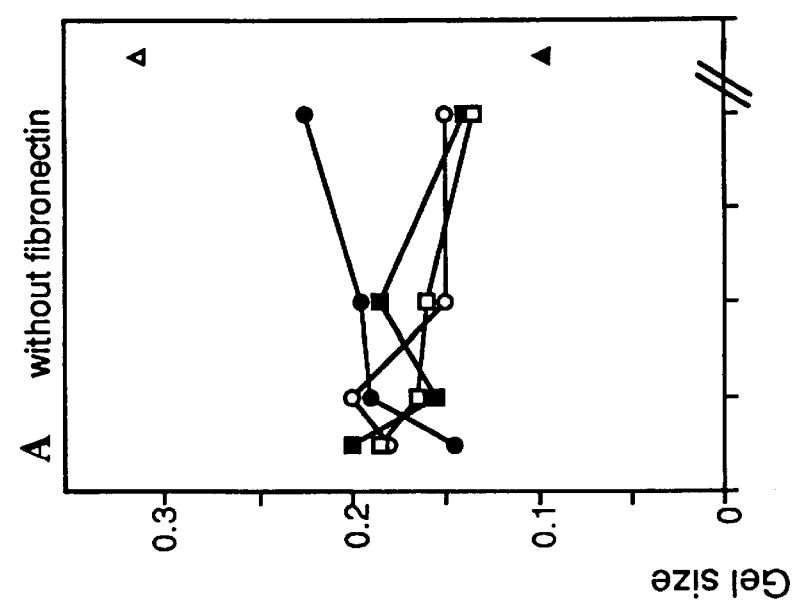
FIG. 11B is a graph showing the gel size for collagen gels, prepared in the presence of fibronectin, which were seeded with fibroblasts. Fibronectin-derived peptides were added to wells as indicated. After 7 days, the gels were measured to determine the extent of contraction.
Figures 11C, 11D:
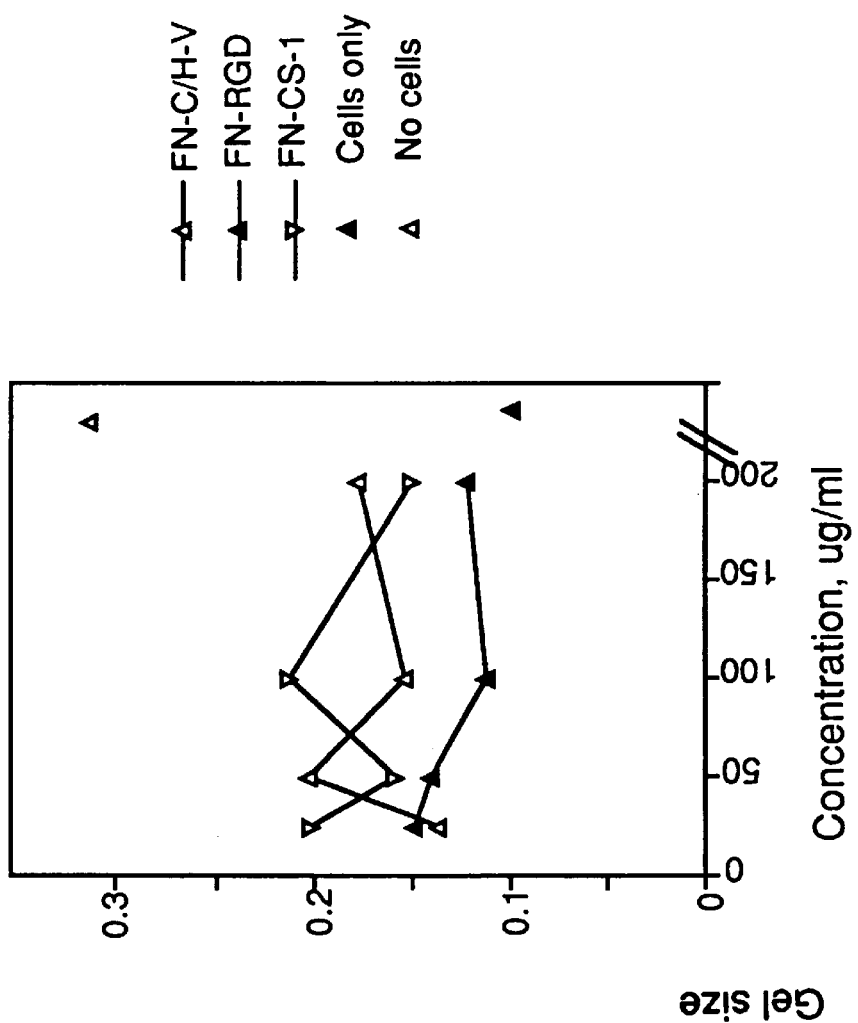
FIG. 11C is a graph showing the gel size for collagen gels, prepared in the absence of fibronectin, which were seeded with fibroblasts. Fibronectin-derived peptides were added to wells as indicated. After 7 days, the gels were measured to determine the extent of contraction.
FIG. 11D is a graph showing the gel size for collagen gels, prepared in the presence of fibronectin, which were seeded with fibroblasts. Fibronectin-derived peptides were added to wells as indicated. After 7 days, the gels were measured to determine the extent of contraction.

Fifty thousand rabbit dermal fibroblasts were suspended in 250 μl of fibroblast assay medium and mixed with 250 μl of Vitrogen and dispensed into the wells of a 48-well plate. The cells were preincubated with the desired polypeptide concentration (25, 50, 100, or 200 ug/ml) for one hour at 37° C. before mixing with the Vitrogen. Gelling occurred within 20 minutes after transfer of the mix of cell suspension and Vitrogen into an incubator at 37° C. with 5% $CO_2$. The gels were overlaid with 250 μl of growth medium. All conditions were tested in duplicate wells. After 24 hours, the gels were detached from the sides of the wells by sweeping with a 27-gauge needle inserted at the interface between the plastic well and the gel (FIGS. 6–8).

Contraction of collagen gels was quantitated by use of planimetry. The gels were observed daily over the seven day period following detachment for evidence of contraction. The plates were photographed at the end of the seven days to record the amount of contraction. The contraction was measured by recording the area of each gel in each well off the photograph using a computer scanner. The area of the gels with polypeptide was compared to the area of the gels without the polypeptide. Planimetry is a two-dimensional measurement. Since gel contraction occurs in three dimensions, planimetry does not measure the full extent of gel contraction. The planimetry measurements accordingly underestimate the degree of contraction that actually occurred.

EXAMPLE 4

In vivo Model—Proliferative Vitreoretinopathy in Rabbits

The rabbit model for proliferative vitreoretinopathy is described in Thresher et al., *Graefe's Arch. Clin. Exp. Ophthalmol.*, 221, 192–198 (1984). Adult Dutch Belted rabbits of both sexes were used in the study. All animals were treated according to ARVO Animal Use Guidelines. All eyes were examined prior to initiation of a study and only clinically normal animals were used.

The rabbits were anesthetized using an intramuscular injection of a mix of ketamine (30 mg/kg) and xylazine (5 mg/kg). Pupils were dilated with Mydriacyl (Tropicamide) 1% and Neosynephrine 2.5% topical drops. Topical conjunctival anesthesia was provided with Proparacaine ok drops. All procedures were performed in an approved animal surgical facility. A transscleral cryopexy application was placed in the inferior peripheral retina to create a chorioretinal adhesion at this location. This site was used for subsequent intraocular injections, preventing iatrogenic retinal tears at the injection site. An intravitreal injection of 0.4 cc millipore-filtered 100% perfluoropropane gas was administered to produce a gas compression vitrectomy. Once the expansile gas bubble had absorbed, $5-10 \times 10^4$ dermal rabbit fibroblasts with or without 200 μg of polypeptide (injection volume–0.1 cc) were injected through a 27 gauge needle into the vitreous cavity. Under indirect ophthalmoscopic visualization, the tip of the needle was placed over the optic nerve head and the cells were injected in this location.

The animals were then observed for the development of proliferative vitreoretinopathy. The final stage of retinal detachment was scored from 0 to 7 using the standard grading scale shown below (see Hida et al., *Graefe's Arch. Clin. Exp. Ophthalmol.*, 225, 1763–1769 (1991)).

| Stage # | Status of Retina |
|---|---|
| 0 | Normal |
| 1 | Surface wrinkling |
| 2 | Mild pucker |
| 3 | Severe pucker |
| 4 | Elevated pucker |
| 5 | Partial retinal detachment |
| 6 | Low retinal detachment |
| 7 | Total retinal detachment |

Retinal photographs were taken with a wide field fundus camera (Canon) to document the final stage of retinal detachment. Animals were sacrificed while under deep anesthesia with an intravenous injection of 1 cc of euthanasia solution. The eyes were then immediately enucleated, fixed in 10% formalin, paraffin embedded, sectioned at 7 microns, and stained with hematoxylin and eosin for histology.

Polypeptide Toxicity

The toxicity of the polypeptides was determined by three techniques:

ERG. Electroretinograms (ERG) were carried out as a functional indicator of toxicity of a polypeptide treatment. Polypeptides were injected at 200 ug and 400 ug (twice the dose that inhibited proliferative vitreoretinopathy), and ERG measurements were performed three times in each eye at various times post-injection (1 hr to 6 weeks).

Clinical observations. Observation by indirect ophthalmoscopy and slit lamp examination were performed to probe for evidence of toxicity.

Histology. Following ERG and clinical observations, the eyes were immediately enucleated, fixed in 10% formalin, paraffin embedded, sectioned at 7 microns, and stained with hematoxylin and eosin.

EXAMPLE 5

In vitro Collagen Gel Shrinkage Assays

Controls

The collagen gels were cast with or without the incorporation of 25 ug/ml of fibronectin. Control assays showed that in the absence of fibroblasts there was no contraction, and that addition of fibronectin without cells also gave no contraction (see FIGS. 9A, 9B, 10A, 10B and 11A–11D). In other controls, we found that gamma irradiated (10,000R) fibroblasts did not cause gel contraction, nor did fibroblasts pretreated with mitomycin C (data not shown). These controls using deactivated cells indicate that cell growth and proliferation are required to effect gel shrinkage.

Polypeptide Data

The ability of a number of synthetic polypeptides derived from laminin (FIGS. (9A and 9B), type IV collagen IV (FIGS. 10A and 10B), or fibronectin (FIGS. 11A–11D) to inhibit fibroblast-mediated contraction was examined in the collagen gel shrinkage model. These assays were carried out as described above using collagen gels cast with and without fibronectin. The results demonstrate that laminin polypeptide R37 and type IV collagen polypeptide Hep-II had the most potent inhibitory effects on contraction (see Tables II and III). Inhibition of gel contraction was also observed with laminin polypeptide R26 and fibronectin polypeptide FN-C/H-IV. In contrast, laminin polypeptide R38 and type IV collagen polypeptide IV-H1 were frequently found to promote contraction. Gels cast in the presence of fibronectin exhibited more fibroblast-mediated shrinkage than gels of collagen alone (see FIGS. 9A, 9B, 10A, 10B and 11A–11D).

TABLE II

Inhibition of Fibroblast-mediated Collagen Gel Contraction by Synthetic Peptides from Laminin

| Laminin Peptide | Contraction |
| --- | --- |
| R37 (GD-1) | 12% |
| R38 (GD-2) | 74% |
| R26 (GD-3) | 45% |
| R35 (GD-5) | 63% |
| None | 67% |

In these representative experiments, done on separate days, rabbit dermal fibroblasts suspended in growth medium were mixed with Vitrogen (bovine type I collagen) and placed in 48-well plates at a concentration of 100,000 cells per well. The cells were preincubated for 1 hr with 200 ug of the laminin peptides. Gels with or without fibroblasts served as controls. Computer planimetry was used to calculate the surface area of the gels at day 7. In each case, gels without fibroblasts did not contract and served as negative controls (0% contraction).

TABLE III

Inhibition of Fibroblast-mediated Collagen Gel Contraction by Synthetic Peptides from Type IV Collagen

| Type IV Collagen Peptide | % Contraction |
| --- | --- |
| Hep-I | 33% |
| Hep-II | 3% |
| Hep-III | 33% |
| IV-H1 | 72% |
| None | 36% |

In these representative experiments, done on separate days, rabbit dermal fibroblasts suspended in growth medium were mixed with Vitrogen (bovine type I collagen) and placed in 48-well plates at a concentration of 100,000 cells per well. The cells were preincubated for 1 hr with 200 ug of the type IV collagen peptides. Gels with or without fibroblasts served as controls. Computer planimetry was used to calculate the surface area of the gels at day 7. In each case, gels without fibroblasts did not contract and served as negative controls (0% contraction).

Toxicity Studies

Figure 12A:
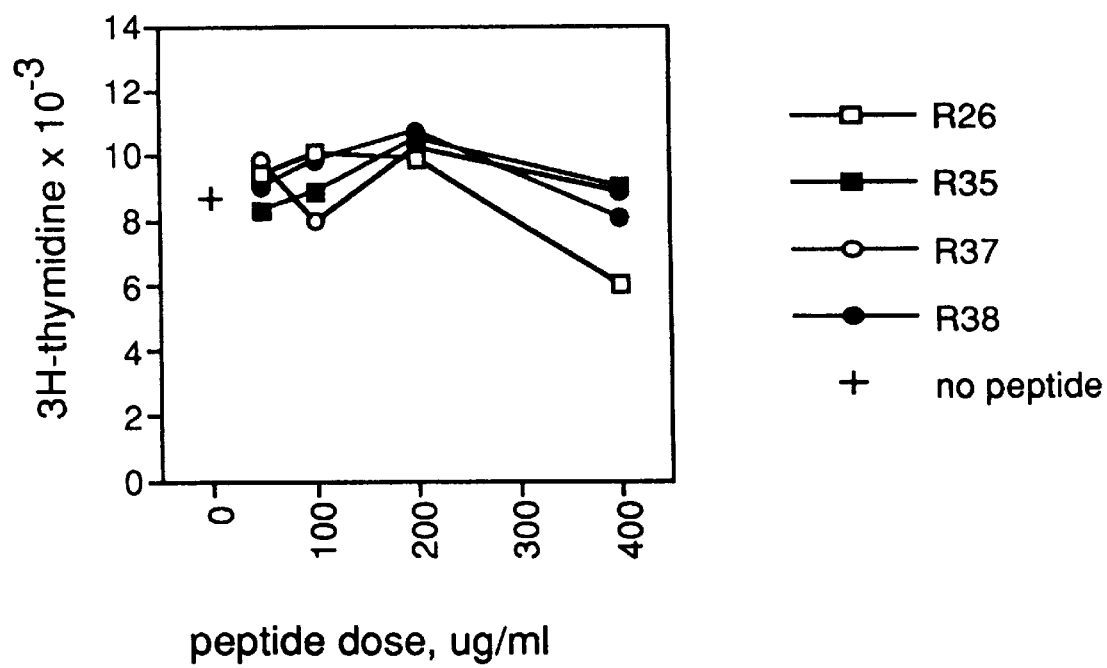
FIG. 12A is a graph showing $^3$H-thymidine incorporation into fibroblasts seeded into 96-well tissue culture plates. The fibroblasts were incubated with the indicated laminin-derived peptides. After 2 days, $^3$H-thymidine was added and the wells were harvested and counted. Each point is the average of duplicate assays. The amount of inhibition of $^3$H-thymidine incorporation by a polypeptide is an in vitro indicator of the toxicity of that polypeptide.
Figure 12B:
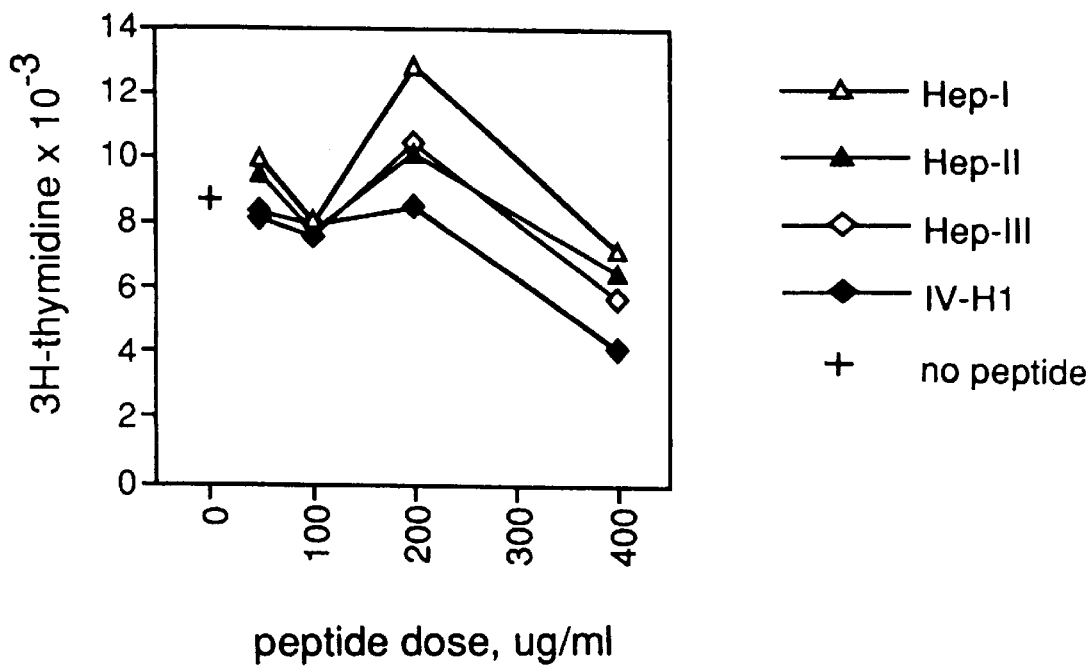
FIG. 12B is a graph showing $^3$H-thymidine incorporation into fibroblasts seeded into 96-well tissue culture plates. The fibroblasts were incubated with the indicated type IV collagen-derived peptides. After 2 days, $^3$H-thymidine was added and the wells were harvested and counted. Each point is the average of duplicate assays. The amount of inhibition of $^3$H-thymidine incorporation by a polypeptide is an in vitro indicator of the toxicity of that polypeptide.
Figure 13:
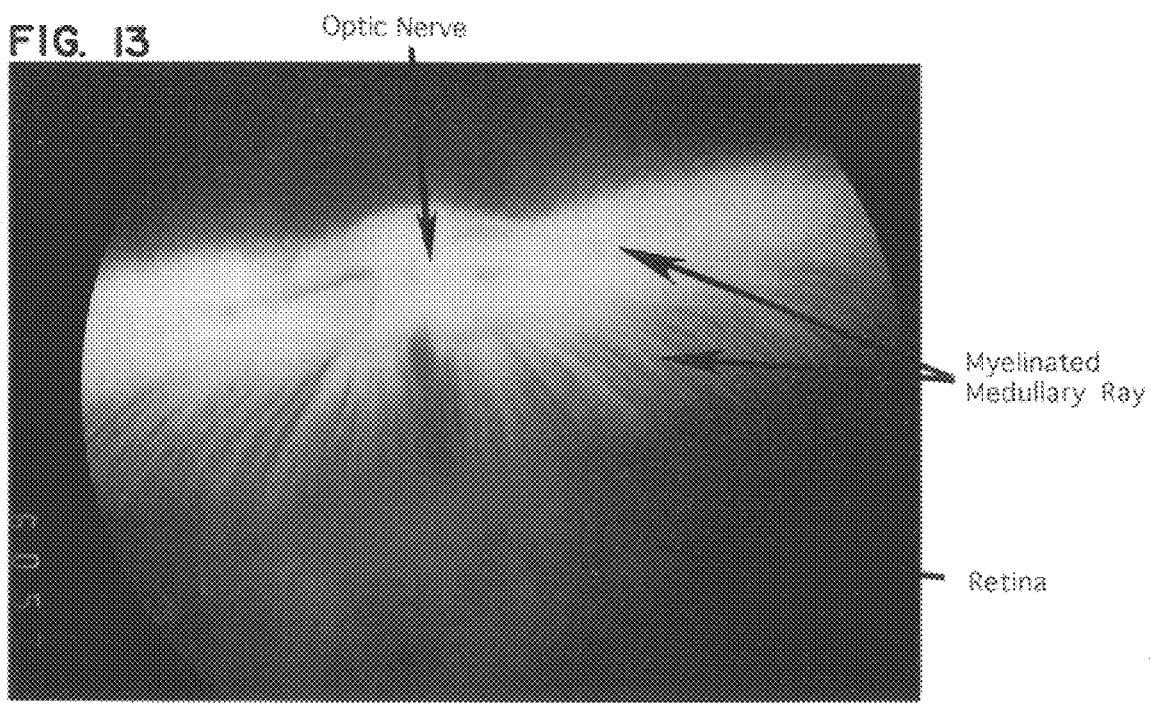
FIG. 13 is a fundus photograph of a normal rabbit eye, showing attached retina, optic nerve, and myelinated medullary ray.
Figure 14:
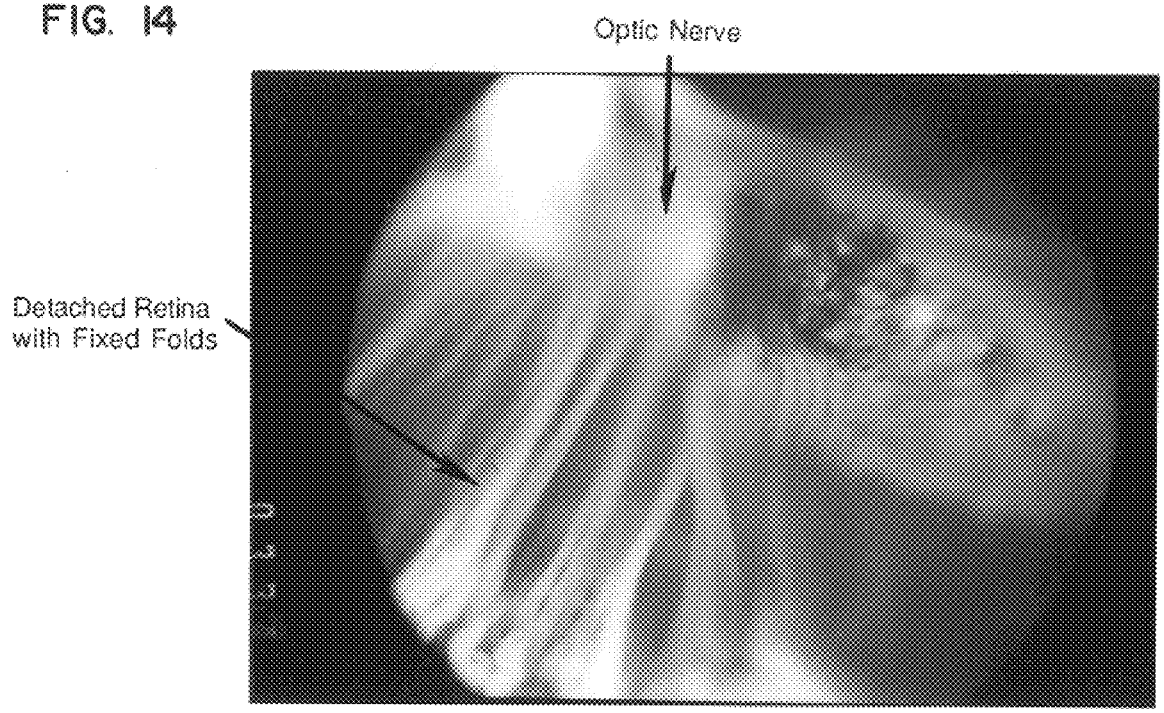
FIG. 14 is a fundus photograph of an experimental total retinal detachment (Stage 7) in the rabbit eye.
Figure 15:
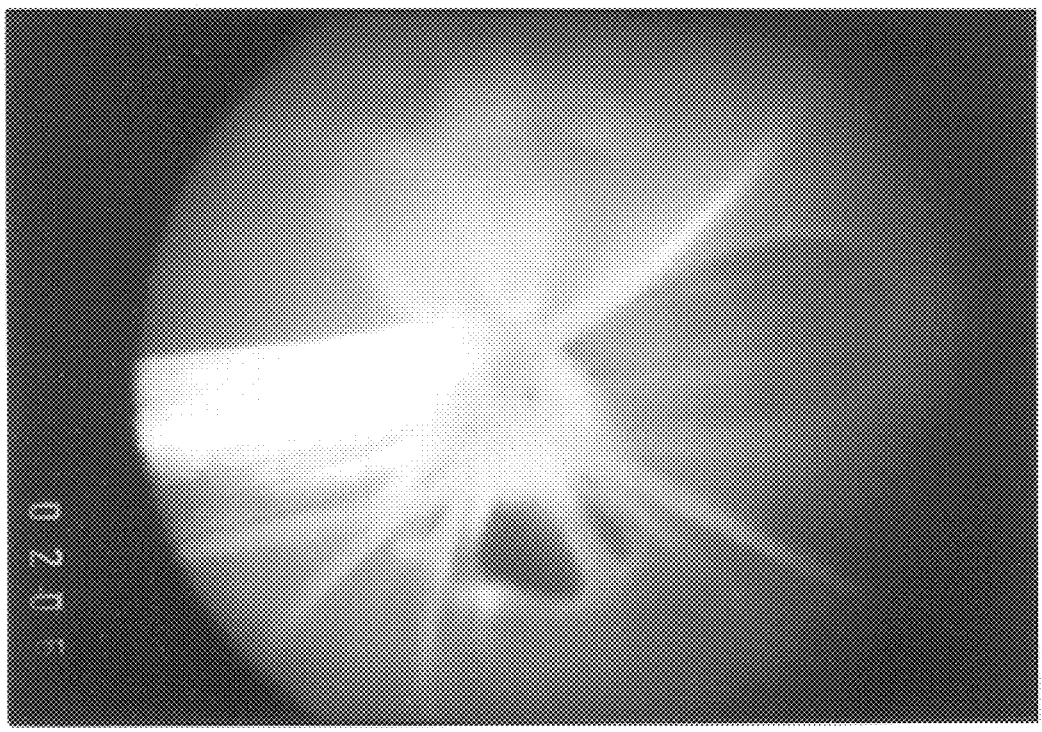
FIG. 15 is a fundus photograph of an untreated rabbit eye, showing Stage 7 total retinal detachment seven days after injection of 100,000 fibroblasts. The atrophic retinal breaks adjacent to the optic nerve and medullary ray and fixed retinal folds posteriorly are evident.
Figure 16:
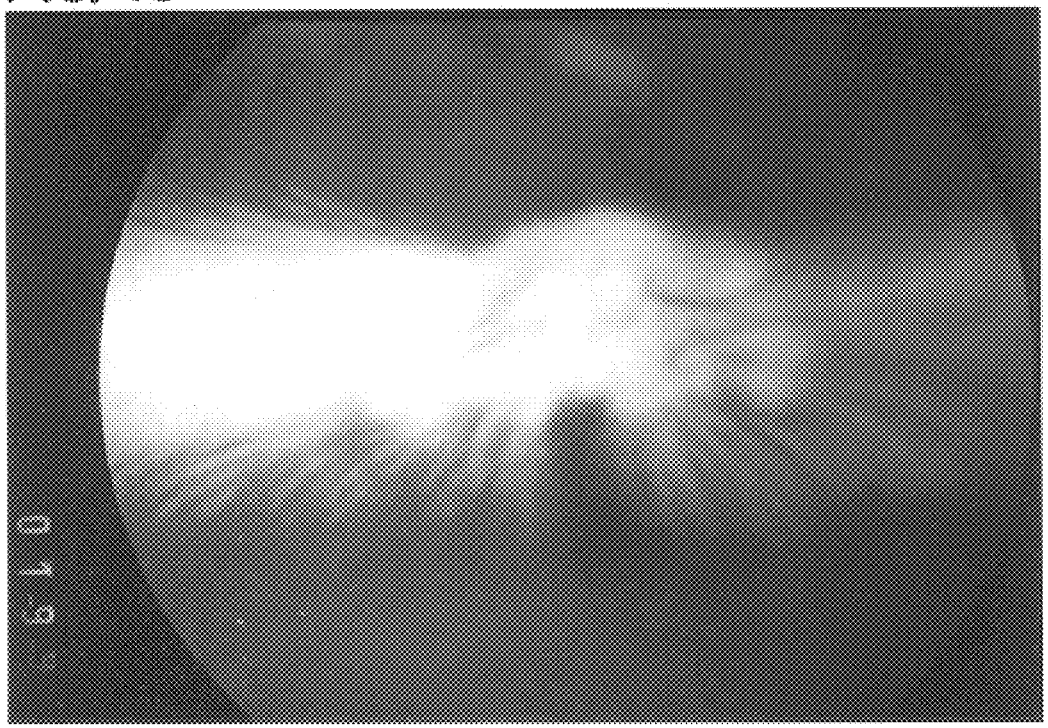
FIG. 16 is a fundus photograph of a rabbit eye which received 200 ug of type IV collagen peptide Hep-II with 100,000 fibroblasts. Seven weeks after fibroblast injection, the retina appeared normal (Stage 0).
Figure 17:
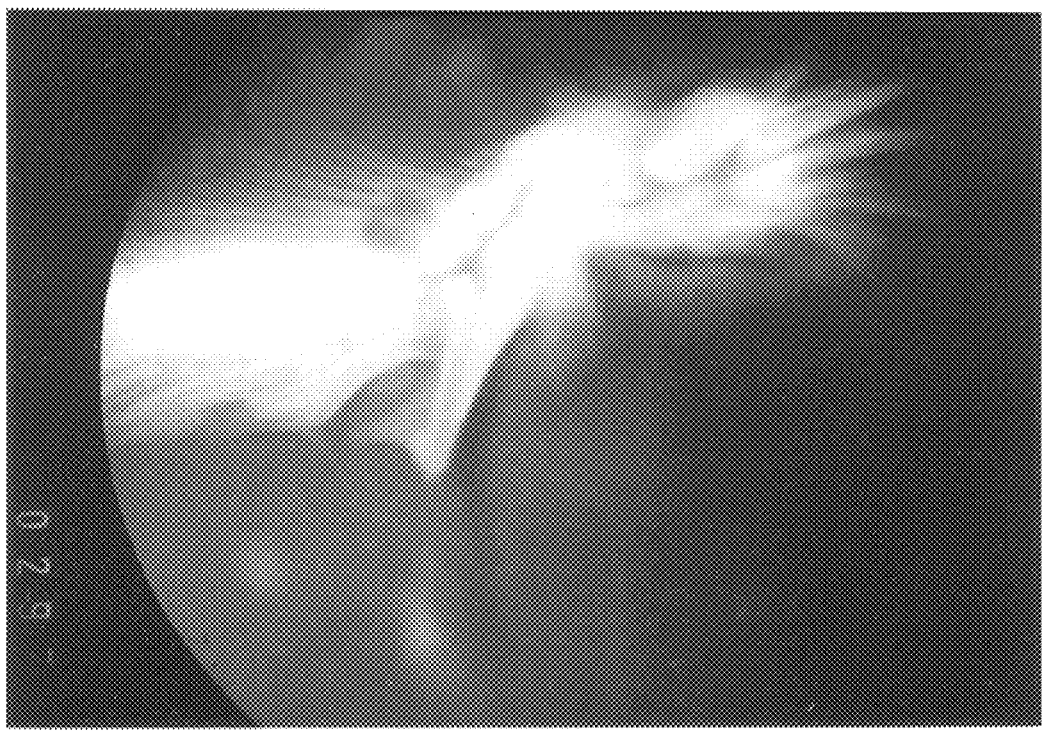
FIG. 17 is a fundus photograph of an untreated rabbit eye, showing Stage 6 retinal detachment development 6 days after injection of 100,000 fibroblasts. Partial retinal detachment along the medullary ray with fixed retinal folds adjacent to the disc nasally and temporally is observed.
Figure 18:
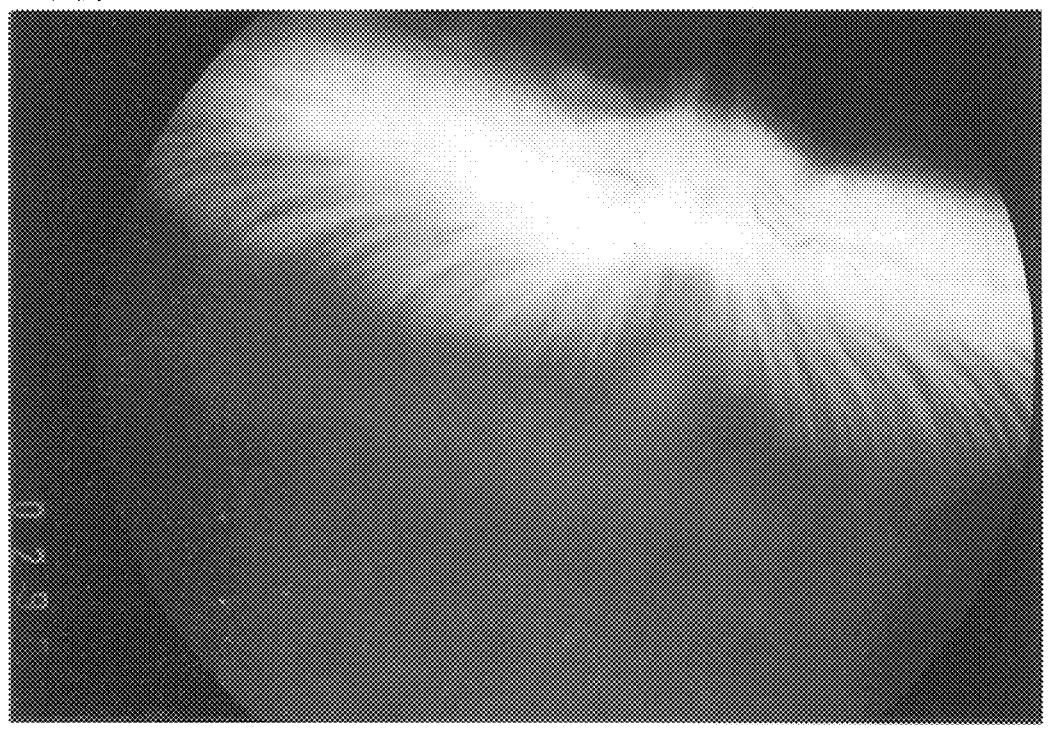
FIG. 18 is a fundus photograph of a rabbit eye which received 200 ug of laminin peptide R37 with 100,000 fibroblasts. Three weeks after fibroblast injection, the retina appeared normal (Stage 0).

The polypeptides were assessed for the presence of growth inhibiting properties by monitoring $^3$H-thymidine incorporation (see FIGS. 12A and 12B). In all of the toxicity studies, cells in all of the wells grew to confluency and appeared healthy. Only minimal effects on growth were observed, and only at a concentration (400 pg/ml) which was well above that used in the gel contraction assay (maximum of 250 µg/ml). None of the polypeptides were found to be cytotoxic.

EXAMPLE 6

In vivo Rabbit Studies
Experimental Proliferative Vitreoretinopathy

Three weeks following peripheral retinal cryopexy and gas compression vitrectomy, rabbit fibroblasts incubated for 1 hr with 200 ug of laminin polypeptide R37, type IV collagen polypeptide Hep-II, or BSS (balanced saline solution; control) were injected intravitreally. One eye of each rabbit received polypeptide incubated fibroblasts and the other eye received the control cells. Eyes were examined every three days, and the degree of retinal detachment was graded on the standard scale described above. Polypeptide R37 and Hep-II both inhibited the degree of retinal detachment (see Table IV and FIGS. 13–18).

TABLE IV

Inhibition of PVR in Rabbits by Synthetic Peptides

| Expt # | Treatment | # Detached Retinas | Total # |
| --- | --- | --- | --- |
| I | Control | 4 (66%) | 6 |
| I | Hep-II | 1 (17%) | 6 |
| II | Control | 2 (40%) | 5 |
| II | R37 (GD-1) | 0 (0%) | 5 |
| III | Control | 7 (100%) | 7 |
| III | R37 (GD-1) | 1 (14%) | 7 |
| IV | Control | 3 (100%) | 3 |
| IV | R37 (GD-1) | 1 (25%) | 4 |

Three weeks following peripheral retinal cryopexy and gas compression vitrectomy, rabbit fibroblasts incubated for 1 hr with 200 ug of laminin peptide R37, type IV collagen peptide Hep-II, or BSS (balanced salt solution; control) were injected intravitreally. One eye of each rabbit received peptide incubated fibroblasts and the fellow eye received the control cells. Eyes were examined every 3 days, and the degree of retinal detachment was graded on a standard scale.
Experiments I and II: 50,000 cells; RD staged at day 21;
Experiment III: 100,000 cells; RD staged at day 7;
Experiment IV: 80,000 cells; RD staged at day 21.

Toxicity Studies

Figure 19:
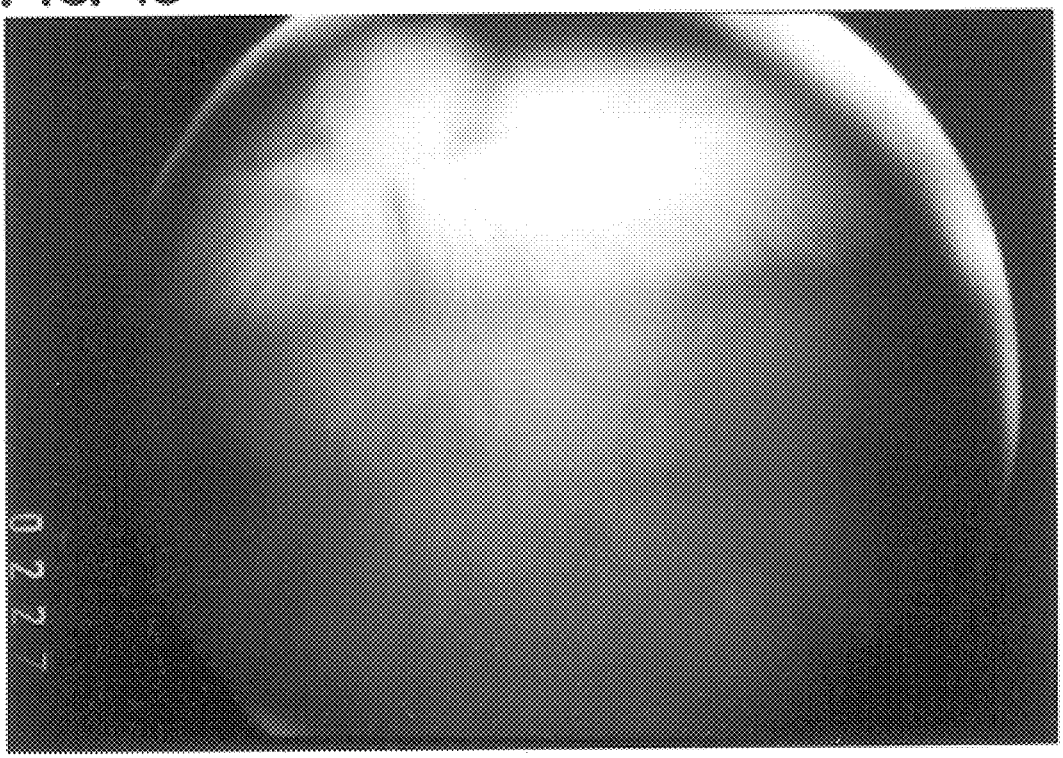
FIG. 19 is a fundus photograph of a rabbit eye showing normal retinal appearance 6 weeks after injection of 0.1 ml of balanced saline solution.
Figure 20:
FIG. 20 is a fundus photograph of a rabbit eye 6 weeks after injection of 200 ug of type IV collagen peptide Hep-II in 0.1 ml. The fundus appearance was indistinguishable from the control eye.
Figure 21:
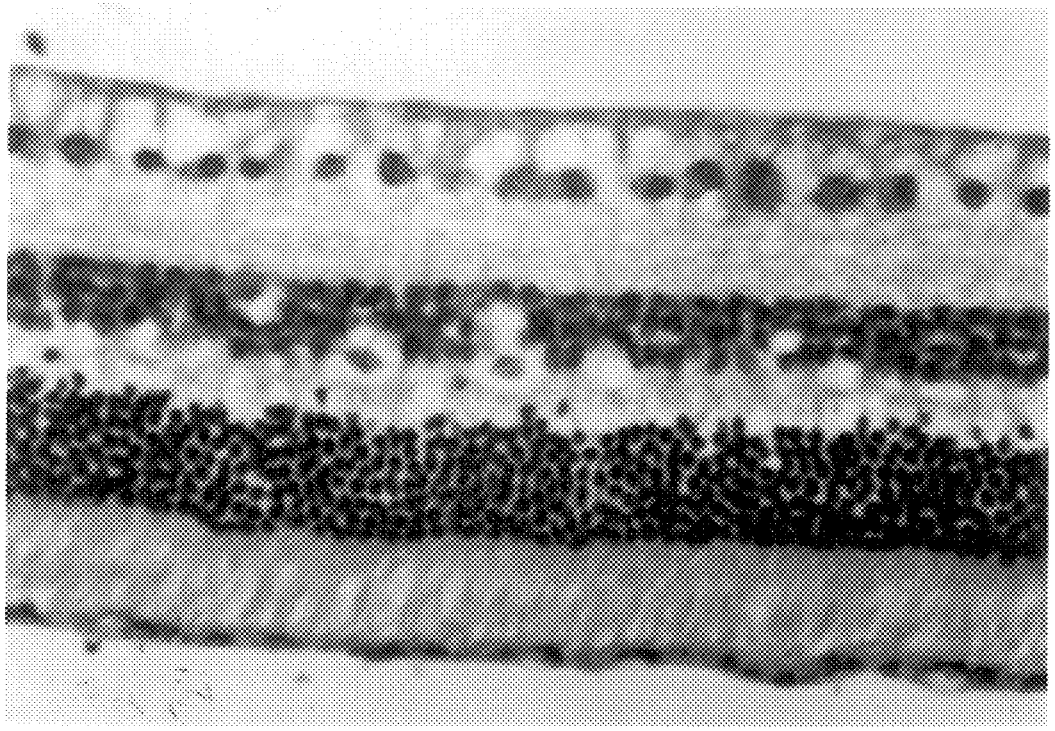
FIG. 21 is a photomicrograph of a control (balanced saline solution treated) rabbit retina, showing normal rabbit retinal histopathology. The retinal pigmented epithelial cells, photoreceptor outer segments and nuclei, inner nuclear layer and ganglion cell layer all appear normal (original magnification×200).
Figure 22:
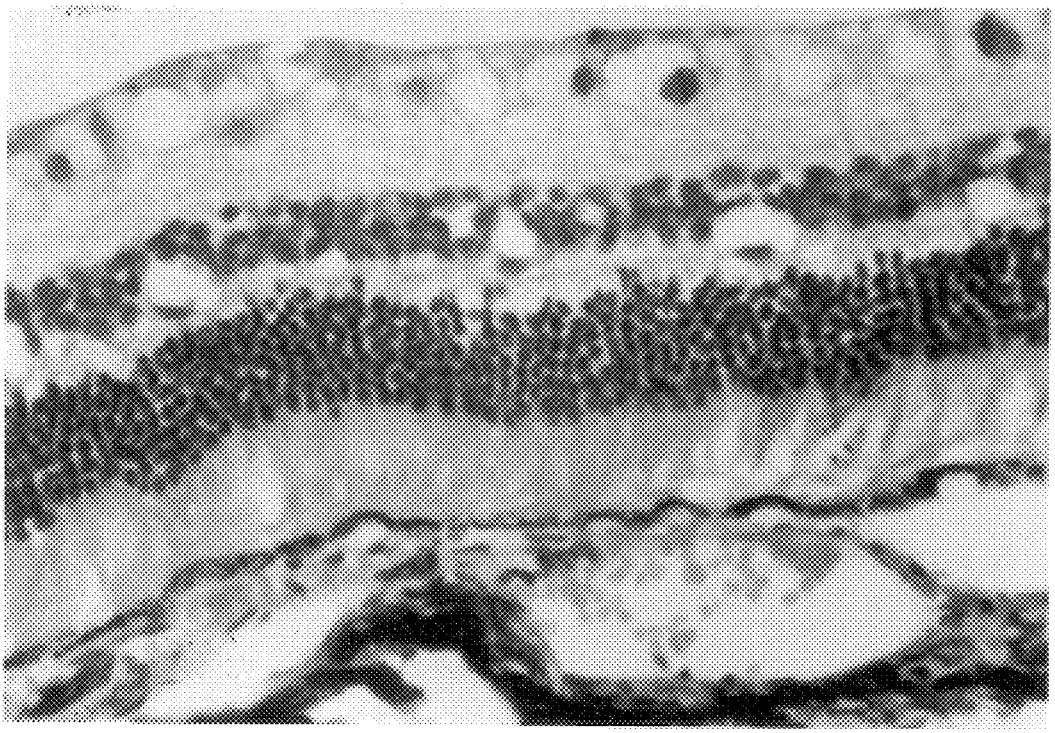
FIG. 22 is a photomicrograph of an experimental rabbit retina, showing normal rabbit retinal histopathology weeks following injection of 400 ug of laminin peptide R37. The retinal pigmented epithelial cells, photoreceptor outer segments and nuclei, inner nuclear layer and ganglion cell layer all appear normal (original magnification×200).
Figure 23A:
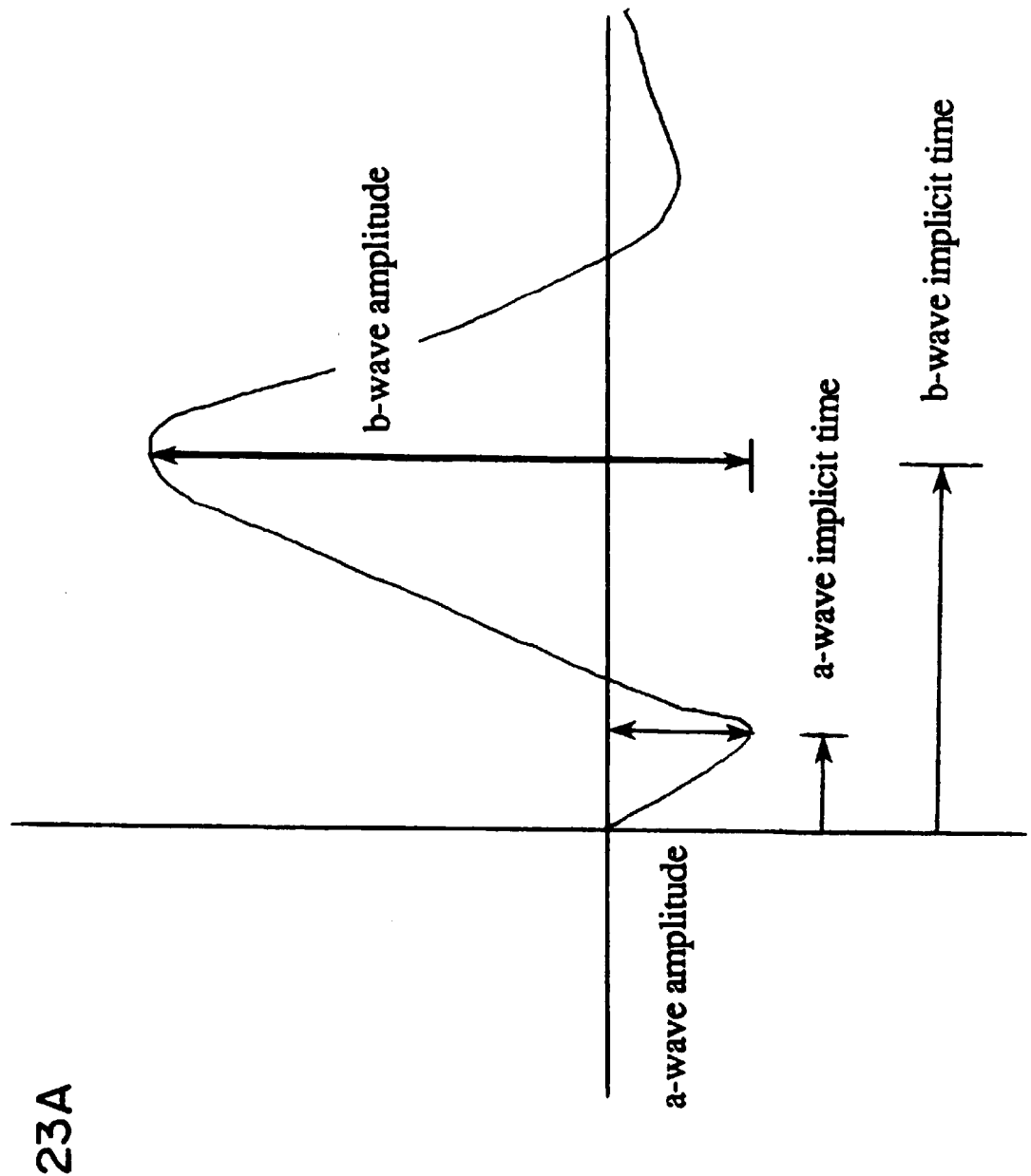
FIG. 23A is a diagrammatic representation of an electroretinogram (ERG) of a rabbit eye used to illustrate the parameters that are measured.
Figure 23B:
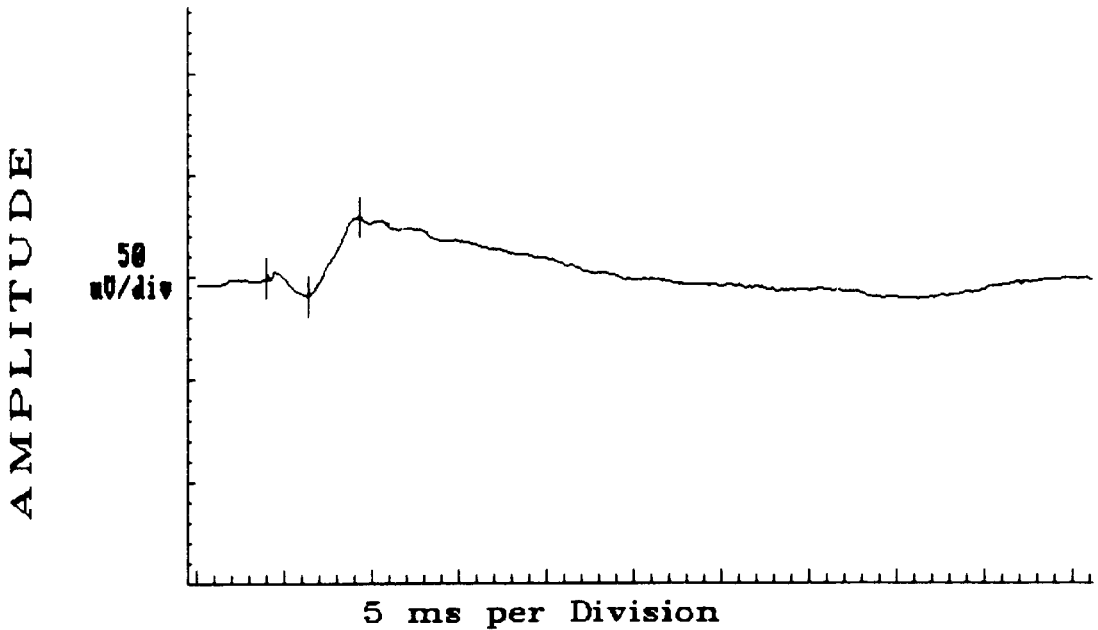
FIG. 23B is a graph showing an ERG of a rabbit eye prior to injection of type IV collagen peptide Hep-II.
Figure 23C:
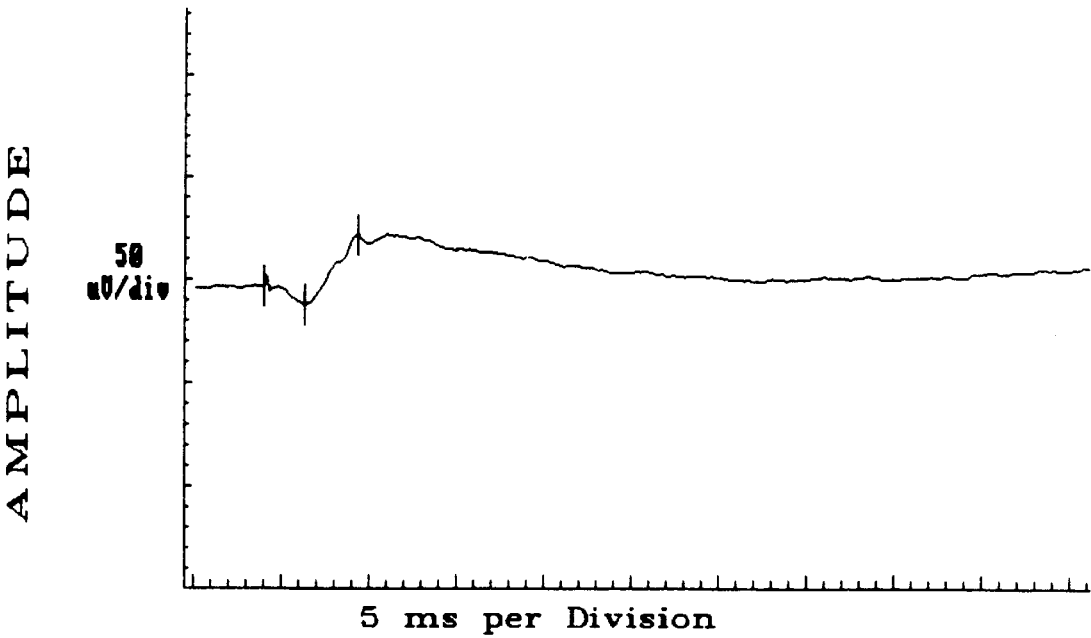
FIG. 23C is a graph showing an ERG of a rabbit eye 24 hr following injection of 400 ug of type IV collagen peptide Hep-II.
Figure 24A:
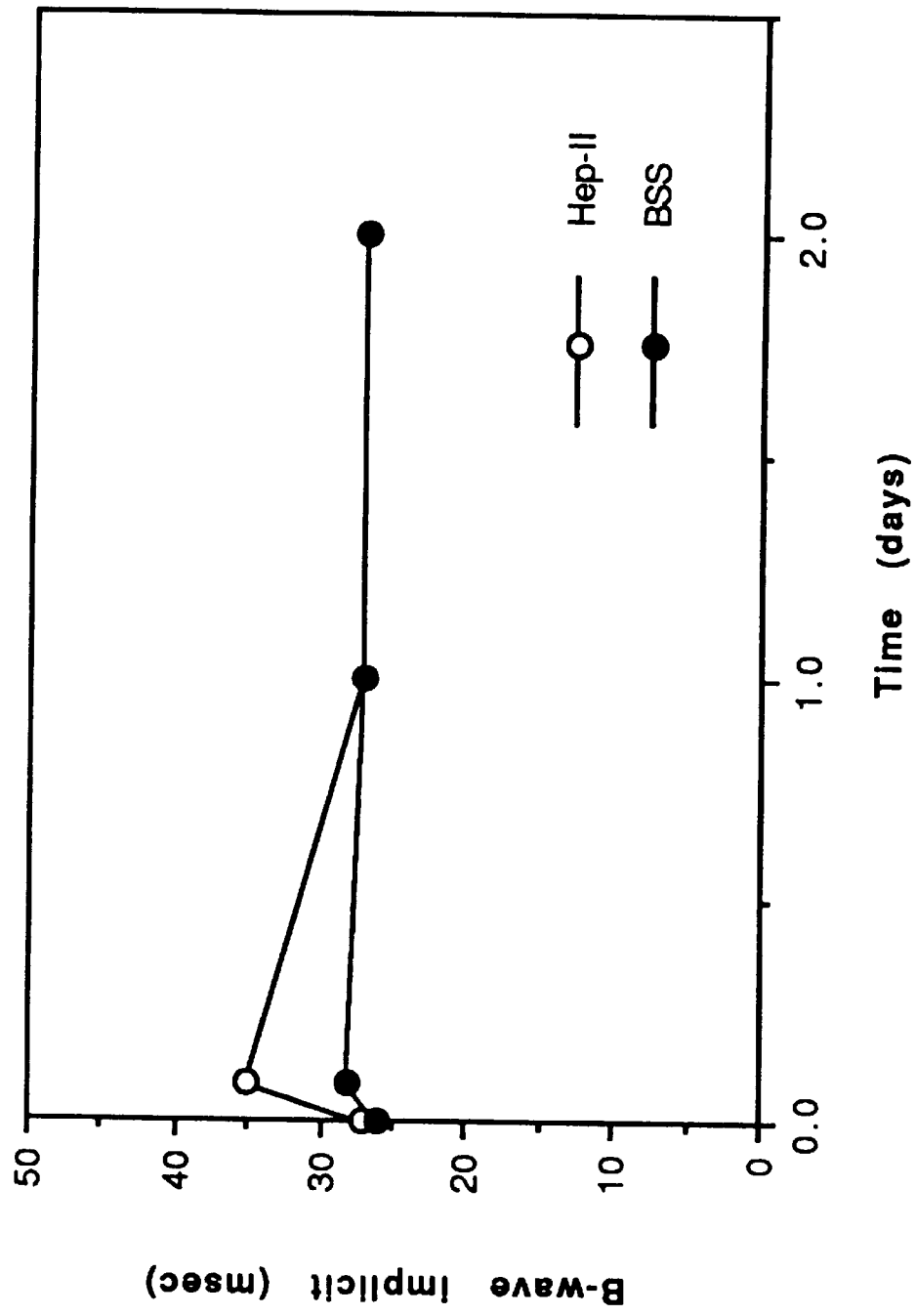
FIG. 24A is a graph showing a B-wave implicit from ERG data of a rabbit eye in the presence and absence of 400 ug of type IV collagen peptide Hep-II.
Figure 24:
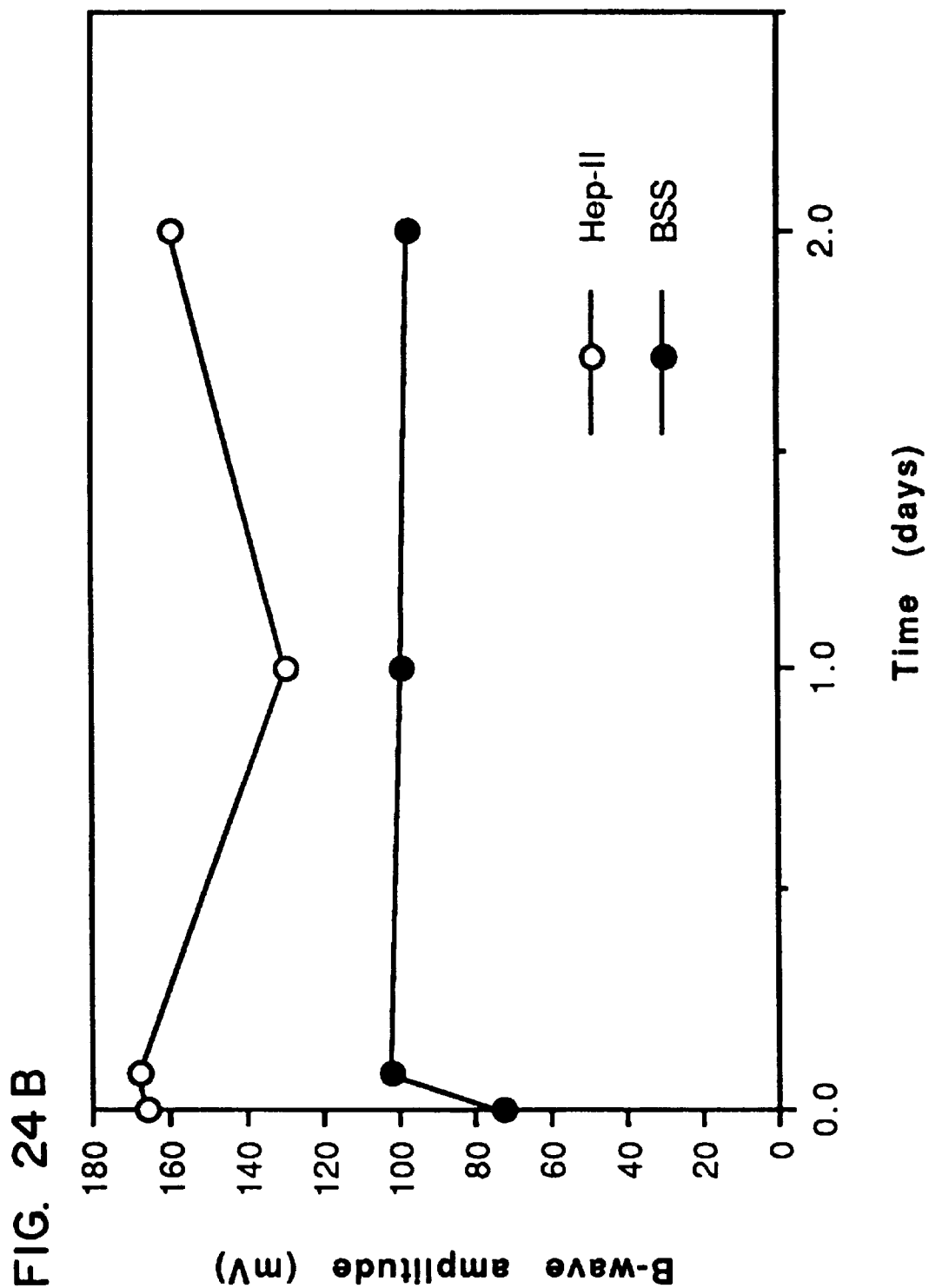
FIG. 24B is a graph showing a B-wave amplitude from ERG data of a rabbit eye in the presence and absence of 400 ug of type IV collagen peptide Hep-II.
Figure 25A:
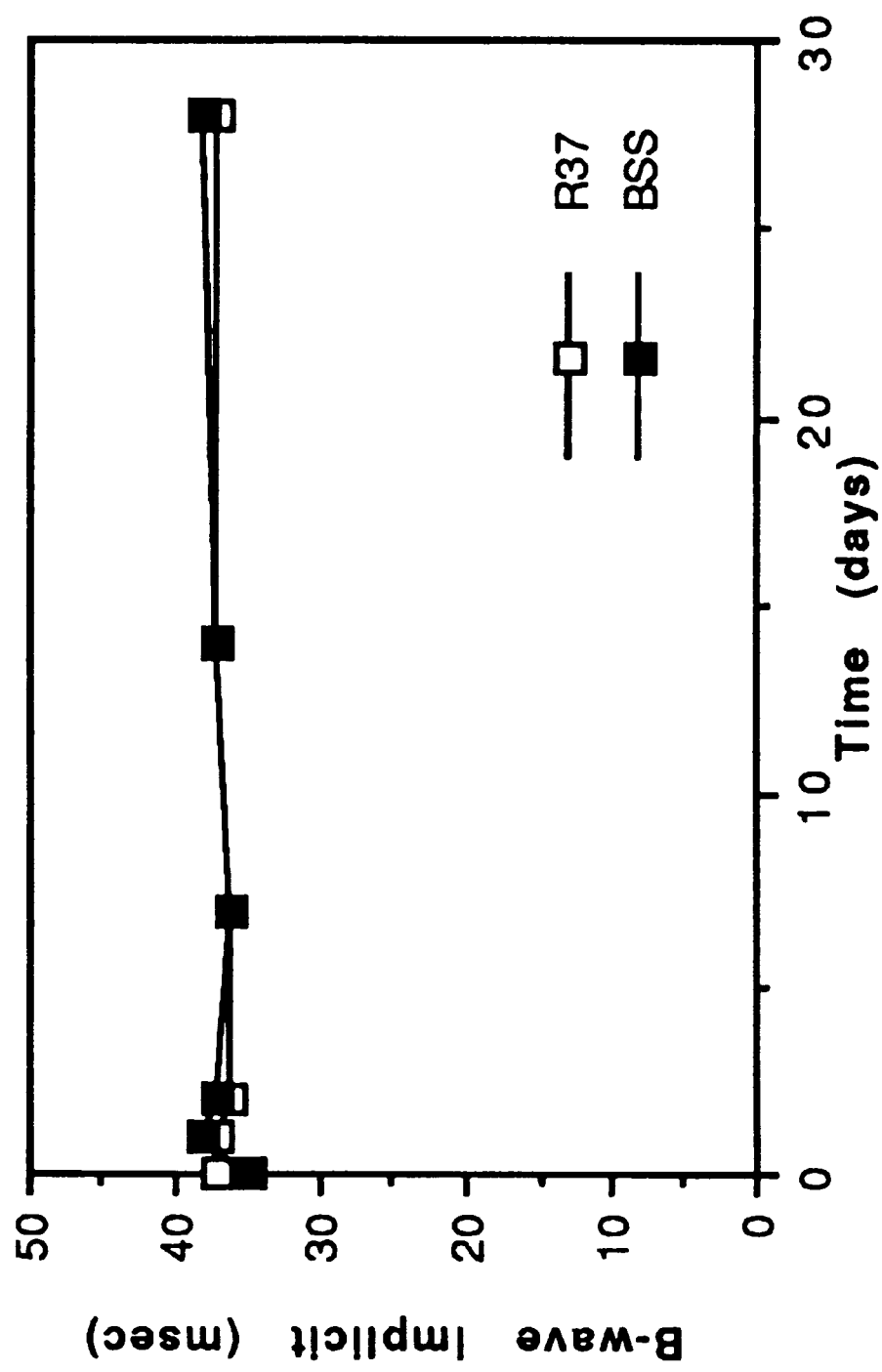
FIG. 25A is a graph showing a B-wave implicit from ERG data of a rabbit eye in the presence and absence of 200 ug of laminin peptide R37.
Figure 25B:
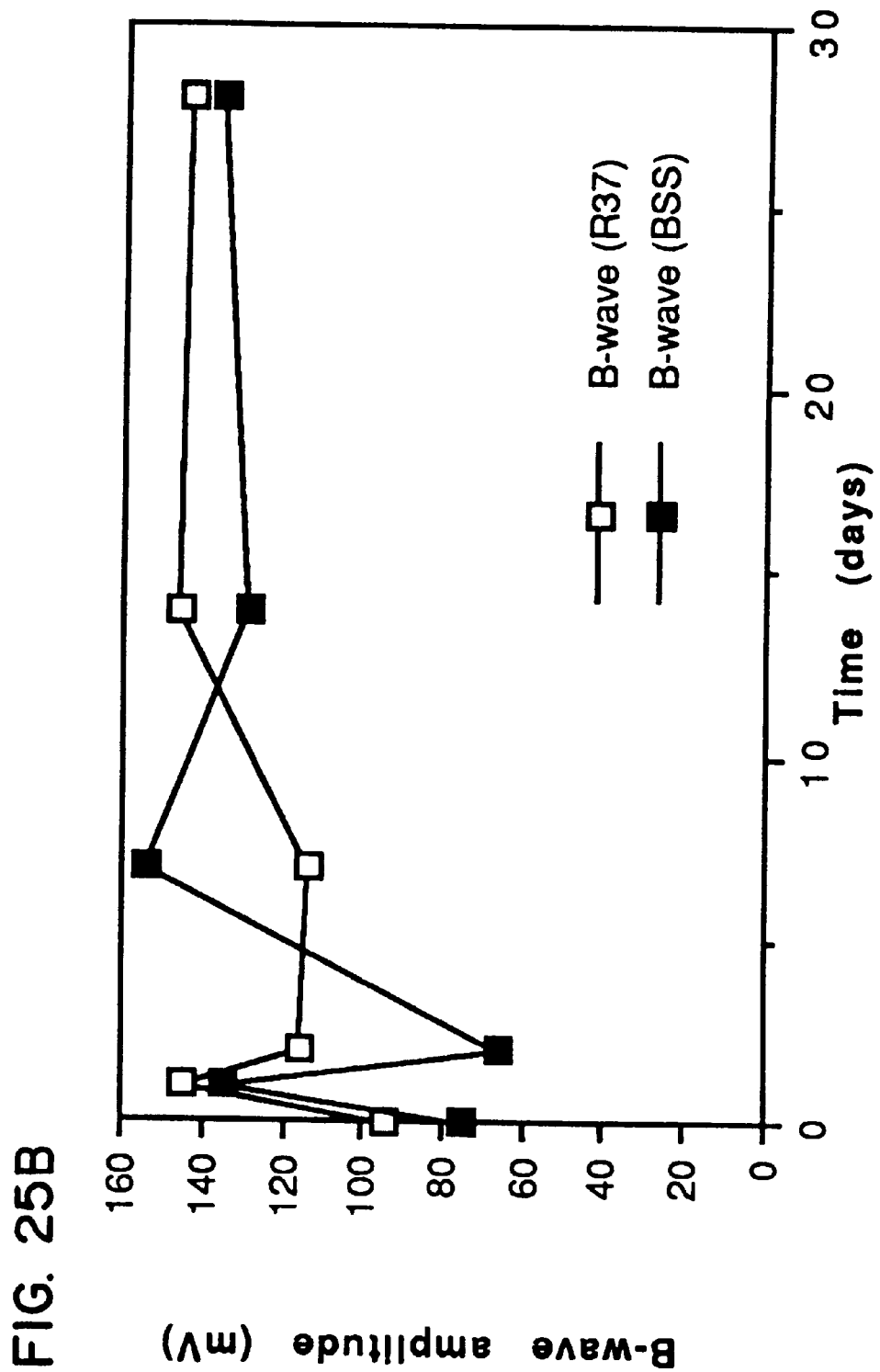
FIG. 25B is a graph showing a B-wave amplitude from ERG data of a rabbit eye in the presence and absence of 200 ug of laminin peptide R37.

No toxic effects were seen by clinical observations (FIGS. 19–20), histopathology (FIGS. 21–22), or ERG (FIGS. 23A–23C, 24A, 24B, 25A and 25B) following intravitreal injection of 200 ug or 400 ug of either polypeptide R37 or Hep-II.

EXAMPLE 7

Preparation of Polypeptide Conjugates

The polypeptides of the present invention may be coupled to a carrier molecule such as human albumin (HA) by dissolving equal amounts of a lyophilized polypeptide (2–10 mg) and HA in a small volume of water (0.5–2 ml). In a second test tube, 1-ethyl-3-(3-dimethylaminopropyl)-carbodiimide hydrochloride (EDC; ten times the amount of polypeptide) is dissolved in water (300 µl). The EDC solution is added to the polypeptide/OA mixture and rotated for 2–18 hours at 4° C. The mixture is then dialyzed into 4 liters of phosphate buffered saline (PBS; pH 7.4), changing dialysis several times. A polypeptide/HA conjugate prepared by this procedure typically contains about 4 to 5 polypeptides per HA molecule as determined by radiolabelling the polypeptide fragments prior to coupling and evaluating the amount bound after coupling.

EXAMPLE 8

In vitro Model—Fibroblast Proliferation

The failure of gluacoma treatment by filtration surgery is most often caused by scarring. Scarring requires fibroblast proliferation and fibrosis of the subconjunctive space. Proliferation of rabbit conjunctival fibroblasts was studied using the tritiated thymidine assay, which serves as an in vitro model of fibroblast proliferation in the rabbit eye (see Invest. Ophthalmol. Vis. Sci., 31, 1848–1855 (1990)). The ability of synthetic polypeptides derived from ECM molecules to inhibit conjuntival fibroblast proliferation was examined in this model.

Rabbit conjunctival fibroblasts were plated into 96-well microtiter plates at 1000 cells/well in 200 microliters of standard fibroblast culture media. Standard fibroblast culture media include Eagle's minimal essential medium containing 15% fetal bovine serum, penicillin G 100 IU/ml, streptomycin 100 µg/ml, and amphotericin B 0.25 µg/ml. Hep-II was added to the wells in concentrations ranging from 1 µg/ml to 1000 µg/ml after removing an equal volume of media to maintain 200 microliters/well. The peptide was used in concentrations of 1, 3, 7, 10, 25, 50, 100, 200, 300, 400, 500, 600, 800 and 1000 microgram/ml (experiments 1–14, respectively in FIG. 26). The tissue culture plates were incubated at 37° C. in a humidified atmosphere of 5% carbon dioxide. Two separate sets experiments were conducted. Each set of experiments was done in replicates of four. In the first set of experiments, tritiated thymidine was added 22 hours prior to each harvesting on days 4, 5, and 8. In the second set of experiments, tritiated thymidine was added 22 hours prior to each harvesting on days 4, 5, and 6. Wells with vehicle but no test compound served as negative controls (experiment #15) and cells with mitomycin-C at 100 µg/ml served as positive controls (experiment #16).

Figure 26:
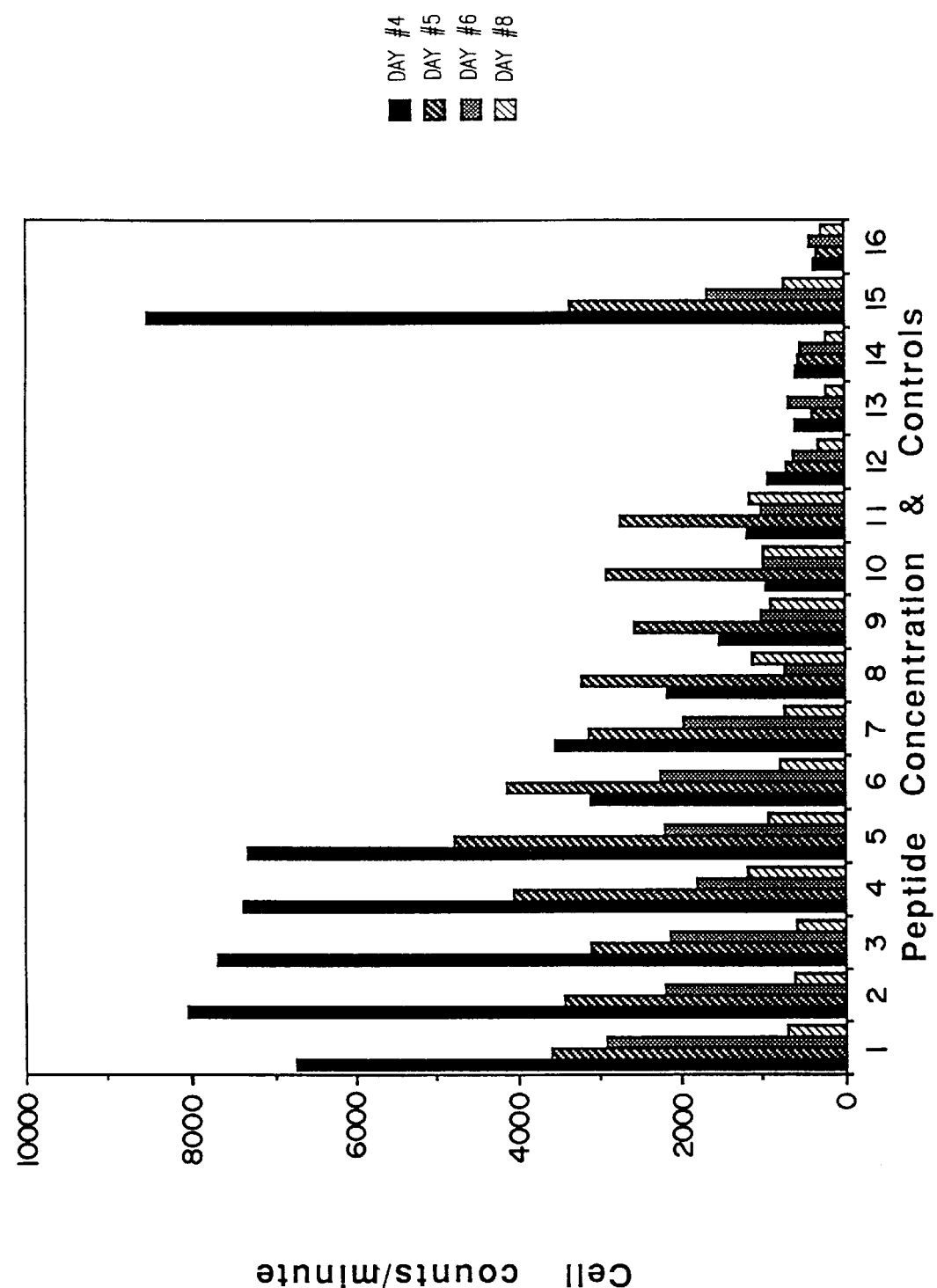
FIG. 26 is a graph showing the effect of Hep-II on the proliferation of rabbit conjunctival fibroblasts as measured by incorporation of tritiated thymidine. Each bar is an average of 4 assays. In addition to the varying concentrations of Hep-II, mitomycin-C and buffer were included as positive and negative controls respectively.

The results illustrated in FIG. 26 are the average of all of the assays from both sets of experiments for days 4 and 5. The results for days 6 and 8 are an average of the assays from the corresponding set of experiments. In summary: thymidine uptake on day 4 in no drug control wells averaged 8537 counts per minute (cpm); wells with mitomycin-C averaged 375 cpm; and the Hep-II treated wells had values of 580 cpm and 589 cpm in 800 microgram/ml and 1000 microgram/ml wells respectively. Similar results were obtained on days 5, 6 and 8. Hep-II is effective in controlling fibroblast proliferation in vitro at concentrations of 800–1000 microgram/ml. The peptide Hep-II is similar to mitomycin-C in controlling fibroblast proliferation at a concentration of 800–1000 microgram/ml in vitro.

EXAMPLE 9

In vivo Model—Filtration Surgery in Rabbits

The rabbit model for filtration surgery is described by Bergstrom TJ, and Skuta GL. et al. in *Arch. Ophthalmol*, 109(12):1725–30, 1991. Two New Zealand white albino rabbits were used in the study. All animals were treated according to ARVO Animal Use Guidelines. All eyes were examined prior to initiation of a study and only clinically normal animals were used.

All the rabbits underwent preoperative examination and the intraocular pressure (IOP) was measured by pneumatonometry (PneumaTonometer, Digilab Model 30R, Cambridge, Mass.). The rabbits were anesthetized using an intramuscular injection of a mix of ketamine (30 mg/kg) and xylazine (5 mg/kg). A posterior lip sclerectomy was then performed on both eyes of each animal during the same period of anesthesia. A lid speculum was placed and a 7–0 polyglactin 910 suture (Vicryl, Ethicon, Somerville, N.J.) on a spatulated needle was passed through the stroma of the superior cornea near the corneoscleral limbus and was used as a traction suture. The superotemporal conjuctiva and Tenon's capsule was incised near the fornix, and the dissection was performed anteriorly to the limbus. The anterior chamber was entered at the filtration site and a 1-mm by 3-mm block of limbal scleral tissue was excised from the posterior lip of the wound with the Kelly-Descemet punch. A peripheral iridectomy was then performed with Vannas scissors and curved jeweler's forceps. Hand-held thermal cautery was used as needed to provide hemostasis. The conjunctiva was closed with a running 10-0 nylon suture. The right eye received subconjunctival injection of the Hep-II dissolved in 0.15 ml distilled water at the end of the filtration surgery and the left eye, which served as the control, received an equal volume of distilled water. These and each of the subsequent injections were made into the area of the bleb. No prophylactic antibiotics, cycloplegic, or corticosteroid was applied to either eye intraoperatively or postoperatively. Postoperative evaluation included examination with a portable slit-lamp biomicroscope, evaluation of the filtering bleb and intraocular pressure measurements obtained with a pneumatonometer. At the end of the study the animals were sacrificed while under anesthesia with an intravenous injection of 1 cc of euthanasia solution.

EXAMPLE 10

In vivo Rabbit Studies of Filtration Surgery Failure

The results of filtration surgery were evaluated by monitoring intraocular pressures and visual inspection of scarring and vascularization. The ability of ability of a synthetic polypeptide to prolong the effect of glaucoma treatment by filtration surgery was examined using the rabbit model. The right eye was treated with subconjunctival injection of 1 milligram of Hep-II dissolved in 0.15 ml of distilled water at the end of filtration surgery and every other day for a total of eight injections. The left eye served as the control and received an equal volume of distilled water on those days. The intraocular pressures (IOP) were checked using a pneumatonometer every other day until day 9 and roughly every other day until day 28 (Table V and FIG. 27). The results were as follows: the IOP in the treated eyes (designated OD in Table V) were lower than the control eyes (designated OS in Table V) throughout the period of the study (28 days) p<0.001. Control eyes reached pre-operative pressures between about day 4 and day 9. Visual inspection indicated that the blebs remained avascular (appeared functional) until day 18 on the treated eyes and until day 10 in the control eyes.

The effect of peptide Hep-II coupled to albumin for the treated eyes and albumin alone for the control eyes was also evaluated. The rabbit eyes that received the peptide/albumin conjugate returned to pre-operative IOP on day 6 as compared to day 3 for the controls. Hep-II peptide, either as a free peptide or in the form of a carrier/peptide conjugate, prolongs the effect of filtration surgery in rabbits in vivo.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

TABLE V

| | Intraocular Pressure of Rabbit Eyes Following Filtration surgery | | | |
|---|---|---|---|---|
| IOP (day#) | Rabbit #3 OD | Rabbit #3 OS | Rabbit #4 OD | Rabbit #4 OS |
| Pre op | 32 | 31 | 34 | 35 |
| Post op #1 | 24 | 22 | 24 | 25 |
| Post op #2 | 30 | 31 | 30 | 25 |
| Post op #3 | 25 | 30 | 22 | 20 |
| Post op #4 | 23 | 32 | 22 | 25 |
| Post op #5 | 22 | 32 | 24 | 30 |
| Post op #6 | 21 | 32 | 23 | 31 |
| Post op #7 | 21 | 30 | 23 | 30 |

TABLE V-continued

Intraocular Pressure of Rabbit Eyes Following Filtration surgery

| IOP (day#) | Rabbit #3 OD | Rabbit #3 OS | Rabbit #4 OD | Rabbit #4 OS |
|---|---|---|---|---|
| Post op #8 | 24 | 31 | 25 | 32 |
| Post op #9 | 22 | 30 | 26 | 37 |
| Post op #13 | 24 | 30 | 27 | 32 |
| Post op #14 | 18 | 28 | 20 | 27 |
| Post op #15 | 25 | 33 | 25 | 35 |
| Post op #16 | 27 | 35 | 28 | 37 |
| Post op #18 | 26 | 34 | 27 | 35 |
| Post op #20 | 25 | 32 | 27 | 34 |
| Post op #21 | 28 | 32 | 32 | 40 |
| Post op #24 | 26 | 32 | 28 | 34 |
| Post op #27 | 33 | 34 | 33 | 36 |
| Post op #28 | 33 | 35 | 35 | 36 |

What is claimed is:

1. A method for treating glaucoma in the eye of a mammal comprising administering to the eye an effective amount for inhibiting scarring of a polypeptide which includes a fragment having the sequence Leu-Ala-Gly-Ser-Cys-Leu-Ala-Arg-Phe-Ser-Thr-Met (SEQ ID NO:3), wherein the polypeptide inhibits fibroblast proliferation.

2. The method of claim 1 wherein the polypeptide suppresses the proliferation within the eye of fibroblast cells.

3. The method of claim 1 wherein the polypeptide suppresses the migration of fibroblast cells.

4. The method of claim 1 wherein the mammal is a human.

5. The method of claim 1 wherein the polypeptide is administered at a concentration ranging from about 0.0001 to about 20 mg/ml.

6. The method of claim 1 wherein administering the polypeptide includes administering the polypeptide in an implant.

7. The method of claim 1 wherein administering the polypeptide includes subconjugatively injecting a solution including the polypeptide.

8. A method for treating glaucoma in a patient comprising administering to said patient an effective amount of a polypeptide of the formula: Leu-Ala-Gly-Ser-Cys-Leu-Ala-Arg-Phe-Ser-Thr-Met [SEQ ID NO:3].

9. A method for treating glaucoma in a mammal comprising: administering to an eye of the mammal an effective amount of a polypeptide/carrier molecule conjugate, wherein the conjugate includes a polypeptide which includes an amino acid sequence having the formula: Leu-Ala-Gly-Ser-Cys-Leu-Ala-Arg-Phe-Ser-Thr-Met [SEQ ID NO:3] bound to each carrier molecule.

10. The method of claim 9 wherein the carrier molecule includes a biological carrier molecule.

11. The method of claim 9 wherein the carrier molecule includes a synthetic carrier molecule.

12. A method for treating proliferative vitreoretinopathy in the eye of a mammal comprising administering to the eye an effective amount for suppressing vitreoretinal scarring of a polypeptide which includes a fragment having the sequence Leu-Ala-Gly-Ser-Cys-Leu-Ala-Arg-Phe-Ser-Thr-Met (SEQ ID NO:3), Lys-Ala-Thr-Pro-Met-Leu-Lys-Met-Arg-Thr-Ser-Phe-His-Gly-Cys-Ile-Lys (SEQ ID NO:5), Lys-Asn-Leu-Glu-Ile-Ser-Arg-Ser-Thr-Phe-Asp-Leu-Leu-Arg-Asn-Ser-Tyr-Gly-Val-Arg-Lys (SEQ ID NO:7), or Ser-Pro-Pro-Arg-Arg-Ala-Arg-Val-Thr (SEQ ID NO:12), wherein the polypeptide suppresses fibroblast-mediated collagen gel contraction.

13. The method of claim 12 wherein the polypeptide suppresses the proliferation within the eye of at least one of fibroblast cells, epithelial cells or glial cells.

14. The method of claim 12 wherein the polypeptide suppresses the migration within the eye of at least one of fibroblast cells, epithelial cells or glial cells.

15. The method of claim 12 wherein the mammal is a human.

16. The method of claim 12 wherein the polypeptide is administered at a concentration ranging from about 0.001 to about 10 mg/ml.

17. The method of claim 12 wherein the polypeptide suppresses the contraction of epiretinal membranes.

18. The method of claim 16 wherein the polypeptide has the sequence Leu-Ala-Gly-Ser-Cys-Leu-Ala-Arg-Phe-Ser-Thr-Met (SEQ ID NO:3).

19. The method of claim 16 wherein the polypeptide has the sequence Lys-Ala-Thr-Pro-Met-Leu-Lys-Met-Arg-Thr-Ser-Phe-His-Gly-Cys-Ile-Lys (SEQ ID NO:5).

20. The method of claim 16 wherein the polypeptide has the sequence Lys-Asn-Leu-Glu-Ile-Ser-Arg-Ser-Thr-Phe-Asp-Leu-Leu-Arg-Asn-Ser-Tyr-Gly-Val-Arg-Lys (SEQ ID NO:7).

21. The method of claim 16 wherein the polypeptide has the sequence Ser-Pro-Pro-Arg-Arg-Ala-Arg-Val-Thr (SEQ ID NO:12).

22. The method of claim 12 wherein the polypeptide is part of a polypeptide/carrier conjugate, wherein said conjugate includes one or more polypeptides bound to a carrier molecule, wherein said polypeptides have a sequence selected from the group consisting of Leu-Ala-Gly-Ser-Cys-Leu-Ala-Arg-Phe-Ser-Thr-Met (SEQ ID NO:3), Lys-Ala-Thr-Pro-Met-Leu-Lys-Met-Arg-Thr-Ser-Phe-His-Gly-Cys-Ile-Lys (SEQ ID NO:5), Lys-Asn-Leu-Glu-Ile-Ser-Arg-Ser-Thr-Phe-Asp-Leu-Leu-Arg-Asn-Ser-Tyr-Gly-Val-Arg-Lys (SEQ ID NO:7), Ser-Pro-Pro-Arg-Arg-Ala-Arg-Val-Thr (SEQ ID NO:12) and mixtures thereof.

23. A method for treating proliferative vitreoretinopathy in the eye of a patient comprising administering to the eye an effective amount for suppressing vitreoretinal scarring of a polypeptide having the sequence Leu-Ala-Gly-Ser-Cys-Leu-Ala-Arg-Phe-Ser-Thr-Met (SEQ ID NO:3).

24. A method for treating proliferative vitreoretinopathy in the eye of a patient comprising administering to the eye an effective amount for suppressing vitreoretinal scarring of a polypeptide having the sequence Lys-Ala-Thr-Pro-Met-Leu-Lys-Met-Arg-Thr-Ser-Phe-His-Gly-Cys-Ile-Lys (SEQ ID NO:5).

25. A method for treating proliferative vitreoretinopathy in the eye of a patient comprising administering to the eye an effective amount for suppressing vitreoretinal scarring of a polypeptide having the sequence Lys-Asn-Leu-Glu-Ile-Ser-Arg-Ser-Thr-Phe-Asp-Leu-Leu-Arg-Asn-Ser-Tyr-Gly-Val-Arg-Lys (SEQ ID NO:7).

26. A method for treating proliferative vitreoretinopathy in the eye of a patient comprising administering to the eye an effective amount for suppressing vitreoretinal scarring of a polypeptide having the sequence Ser-Pro-Pro-Arg-Arg-Ala-Arg-Val-Thr (SEQ ID NO:12).

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 15 amino acids
      (B) TYPE: amino acid
      (D) TOPOLOGY: linear (ii) MOLECULE TYPE: peptide (vi) ORIGINAL SOURCE:
      (B) STRAIN: IV-H1

(xi) SEQUENCE DESCRIPTION: SEQ ID NO:1:

```
Gly Val Lys Gly Asp Lys Gly Asn Pro Gly Trp Pro Gly Ala Pro
 1               5                  10                  15
```

(2) INFORMATION FOR SEQ ID NO:2:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (vi) ORIGINAL SOURCE:
      (B) STRAIN: Hep-I (xi) SEQUENCE DESCRIPTION: SEQ ID NO:2:

```
Thr Ala Gly Ser Cys Leu Arg Lys Phe Ser Thr Met
 1               5                  10
```

(2) INFORMATION FOR SEQ ID NO:3:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (vi) ORIGINAL SOURCE:

(B) STRAIN: Hep-II (xi) SEQUENCE DESCRIPTION: SEQ ID NO:3:

Leu Ala Gly Ser Cys Leu Ala Arg Phe Ser Thr Met
1               5                   10

(2) INFORMATION FOR SEQ ID NO:4:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (vi) ORIGINAL SOURCE:
        (B) STRAIN: Hep-III (xi) SEQUENCE DESCRIPTION: SEQ ID NO:4:

Gly Glu Phe Tyr Phe Asp Leu Arg Leu Lys Gly Asp Lys
1               5                   10

(2) INFORMATION FOR SEQ ID NO:5:

(i) SEQUENCE CHARACTERISTICS:
        (A) LENGTH: 17 amino acids
        (B) TYPE: amino acid
        (D) TOPOLOGY: linear (ii) MOLECULE TYPE: peptide (vi) ORIGINAL SOURCE:
        (B) STRAIN: R37 (GD-1)

(xi) SEQUENCE DESCRIPTION: SEQ ID NO:5:

Lys Ala Thr Pro Met Leu Lys Met Arg Thr Ser Phe His Gly Cys Ile
1               5                   10                  15
Lys (2) INFORMATION FOR SEQ ID NO:6:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (vi) ORIGINAL SOURCE:
        (B) STRAIN: R38 (GD-2)

(xi) SEQUENCE DESCRIPTION: SEQ ID NO:6:

Lys Glu Gly Tyr Lys Val Arg Leu Asp Leu Asn Ile Thr Leu Glu Phe
1               5                   10                  15
Arg Thr Thr Ser Lys
            20

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (vi) ORIGINAL SOURCE:
        (B) STRAIN: R26 (GD-3)

(xi) SEQUENCE DESCRIPTION: SEQ ID NO:7:

```
Lys Asn Leu Glu Ile Ser Arg Ser Thr Phe Asp Leu Leu Arg Asn Ser
  1               5                  10                  15

Tyr Gly Val Arg Lys
             20

(2) INFORMATION FOR SEQ ID NO:8:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (vi) ORIGINAL SOURCE:
        (B) STRAIN: R35 (GD-5)

(xi) SEQUENCE DESCRIPTION: SEQ ID NO:8:

Thr Ser Leu Arg Lys Ala Leu Leu His Ala Pro Thr Gly Ser Tyr Ser
  1               5                  10                  15

Asp Gly Gln (2) INFORMATION FOR SEQ ID NO:9:

(i) SEQUENCE CHARACTERISTICS:
        (A) LENGTH: 19 amino acids
        (B) TYPE: amino acid
        (D) TOPOLOGY: linear (ii) MOLECULE TYPE: peptide (vi) ORIGINAL SOURCE:
        (B) STRAIN: FN-C/H-I (xi) SEQUENCE DESCRIPTION: SEQ ID NO:9:

Tyr Glu Lys Pro Gly Ser Pro Pro Arg Glu Val Val Pro Arg Pro Arg
  1               5                  10                  15

Pro Gly Val (2) INFORMATION FOR SEQ ID NO:10:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (vi) ORIGINAL SOURCE:
        (B) STRAIN: FN-C/H-IIa (xi) SEQUENCE DESCRIPTION: SEQ ID NO:10:

Lys Asn Asn Gln Lys Ser Glu Pro Leu Ile Gly Arg Lys Lys Thr
  1               5                  10                  15

(2) INFORMATION FOR SEQ ID NO:11:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (vi) ORIGINAL SOURCE:
        (B) STRAIN: FN-C/H-III (xi) SEQUENCE DESCRIPTION: SEQ ID NO:11:
```

```
Tyr Arg Val Arg Val Thr Pro Lys Glu Lys Thr Gly Pro Met Lys Glu
1               5                   10                  15
```

(2) INFORMATION FOR SEQ ID NO:12:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (vi) ORIGINAL SOURCE:
        (B) STRAIN: FN-C/H-IV (xi) SEQUENCE DESCRIPTION: SEQ ID NO:12:

```
Ser Pro Pro Arg Arg Ala Arg Val Thr
1               5
```

(2) INFORMATION FOR SEQ ID NO:13:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (vi) ORIGINAL SOURCE:
        (B) STRAIN: FN-C/H-V (xi) SEQUENCE DESCRIPTION: SEQ ID NO:13:

```
Trp Gln Pro Pro Arg Ala Arg Ile
1               5
```

(2) INFORMATION FOR SEQ ID NO:14:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (vi) ORIGINAL SOURCE:
        (B) STRAIN: FN-RGD (xi) SEQUENCE DESCRIPTION: SEQ ID NO:14:

```
Ile Thr Val Ala Tyr Ala Val Thr Gly Arg Gly Asp Ser Pro Ala Ser
1               5                   10                  15
Ser Lys Pro Ile Ser
            20
```

(2) INFORMATION FOR SEQ ID NO:15:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (vi) ORIGINAL SOURCE:
        (B) STRAIN: CS1

(xi) SEQUENCE DESCRIPTION: SEQ ID NO:15:

```
Asp Glu Leu Pro Gln Leu Val Thr Leu Pro His Pro Asn Leu His Gly
1               5                   10                  15
Pro Glu Ile Leu Asp Val Pro Ser Thr
            20                  25
```

(2) INFORMATION FOR SEQ ID NO:16:

(i) SEQUENCE CHARACTERISTICS:
       (A) LENGTH: 4 amino acids
       (B) TYPE: amino acid
       (D) TOPOLOGY: linear (ii) MOLECULE TYPE: peptide (xi) SEQUENCE DESCRIPTION: SEQ ID NO:16:

Arg Gly Asp Ser